(12) United States Patent
Sepetov et al.

(10) Patent No.: US 6,799,120 B2
(45) Date of Patent: Sep. 28, 2004

(54) NONREDUNDANT SPLIT/POOL SYNTHESIS OF COMBINATORIAL LIBRARIES

(75) Inventors: Nikolai F. Sepetov, Los Gatos, CA (US); Olga L. Issakova, Los Gatos, CA (US); Stephen A. Baum, Encinitas, CA (US); James A. Ostrem, Tucson, AZ (US)

(73) Assignee: Nanoscale Combinatorial Synthesis, Inc., Menlo Park, CA (US)

( * ) Notice: Subject to any disclaimer, the term of this patent is extended or adjusted under 35 U.S.C. 154(b) by 723 days.

(21) Appl. No.: 09/776,233

(22) Filed: Feb. 2, 2001

(65) Prior Publication Data

US 2001/0041344 A1 Nov. 15, 2001

Related U.S. Application Data

(60) Provisional application No. 60/180,111, filed on Feb. 3, 2000, provisional application No. 60/180,112, filed on Feb. 3, 2000, provisional application No. 60/180,115, filed on Feb. 3, 2000, and provisional application No. 60/188,937, filed on Mar. 10, 2000.

(51) Int. Cl.[7] .......................... G06F 19/00; C12M 1/00
(52) U.S. Cl. ...................................... 702/19; 435/283.1
(58) Field of Search .......................... 702/19; 435/283.1

(56) References Cited

U.S. PATENT DOCUMENTS

| | | |
|---|---|---|
| 4,631,211 A | 12/1986 | Houghten |
| 5,143,854 A | 9/1992 | Pirrung et al. |
| 5,463,564 A | 10/1995 | Agrafiotis et al. |
| 5,910,655 A | 6/1999 | Skilling |
| 6,017,693 A | 1/2000 | Yates, III et al. |
| 6,147,344 A | 11/2000 | Annis et al. |
| 6,207,370 B1 | 3/2001 | Little et al. |
| 6,207,861 B1 | 3/2001 | Nash et al. |

FOREIGN PATENT DOCUMENTS

WO    WO 97/37953 A1    10/1997

OTHER PUBLICATIONS

Buchardt et al. (2000) "Solid Phase Combinatorial Library of Phosphinic Peptides for Discovery of Matrix Metalloproteinase Inhibitors."*J. Comb. Chem.* 2:624–638.

Database CAPLUS in STN, Chemical Apstracts, No. 133:74284, Carlson, Coby B. et al. "Solid–phase synthesis of acridine–peptide conjugates and their analysis by tandem mass spectrometry." Abstract Org. Lett., 2000 (Abstract only).

(List continued on next page.)

*Primary Examiner*—John S. Brusca
(74) *Attorney, Agent, or Firm*—Christopher C. Sappenfield; Jonathan Alan Quine; Quine Intellectual Property Law Group, P.C.

(57) ABSTRACT

The present invention includes methods for generating combinatorial libraries on solid phase supports in which increased productivity is achieved by pooling all common steps in synthesis without using a tracking or coding system to record the synthetic history of each compound. Methods for generating combinatorial libraries in which containers with random mixtures of solid phase particles are divided and combined together in non-random ways without the exchange of particles between containers are also provided. Various products are optionally produced in multi-stage syntheses according to the invention, such as oligomers and synthetic non-repetitive organic molecules. The methods additionally relate to the identification of each library component without adding extra synthetic, physical, optical, or electronic encoding steps during library synthesis. Combinatorial synthetic systems are also provided.

54 Claims, 7 Drawing Sheets

OTHER PUBLICATIONS

Database CAPLUS in STN, Chemical Apstracts, No. 132:251406, Aubagnac, J–L. et al. "Identification of synthetic by–products in combinatorial libraries using high performance liquid chromatography–electrospray ionization mass spectrometry." Abstract, Comb. Chem. High Throughput Screening, 1999 (Abstract only).

Database CAPLUS in STN, Chemical Apstracts, No. 130:325543, Fitch, Wililiam L. "Analytical methods for quality control of combinatorial libraries." Abstrat, Mol. Diversity, 1999 (Abstract only).

Barnes et al. (1998) *S. Rec. Res. Dev. Org. Chem.* 2:367–379.

Berlin et al. (1997) "Spectrometrically Monitored Selection Experiments–Quantitative Laser Desorption Mass Spectrometry of Small Chemical Libraries," *Chem. Biol.* 4:63–77.

Brummel et al. (1996) "Evaluation of Mass Spectrometric Methods Applicable to the Direct Analysis of Non–Peptide Bead–Bound Combinatorial Libraries," *Anal. Chem.* 68:237–242.

Bunin and Ellman (1992) "A general and expedient method for the solid phase synthesis of 1,4–benzodiazepine derivatives," *J. Amer. Chem. Soc.* 114:10997–10998.

Carrasco et al. (1997) "Direct Monitoring of Organic Reactions on Polymeric Supports," *Tetrahedron Lett.* 38:6331–6334.

Chu et al. (1993) "Using affinity capillary electrophoresis to identify the peptide in a peptide library that binds most tightly to vancomycin," *J. Org. Chem.* 58:648–652.

Czarnik (1997) "Encoding methods for combinatorial chemistry," *Curr. Opin. Chem. Biol.* 1:60–66.

Davis and Swayze (2000) "Automated solid–phase synthesis of linear nitrogen–linked compounds," *Biotechnol. Bioeng.* 71:19–27.

Demirev and Zubarev (1997) "Probing combinatorial library diversity by mass spectrometry," *Anal. Chem.* 69:2893–2900.

DeWitt et al. (1993) "Diversomers': an approach to non-peptide, nonoligomeric chemical diversity," *Proc. Natl. Acad. Sci. USA* 90:6909–6913.

Enjalbal et al., (2000) "Mass spectrometry in combinatorial chemistry," *Mass Spectrom. Rev.* 19:139–161.

Fitch et al. (1994) "High–resolution (1)H NMR in solid–phase organic synthesis," *J. Org. Chem.* 59:7955–7956.

Gao et al. (1996) "Screening derivatized peptide libraries for tight binding inhibitors to carbonic anhydrase II by electrospray ionization mass spectrometry," *J. Med. Chem.* 39:1949–1955.

Geysen et al. (1986) "A priori delineation of a peptide which mimics a discontinuous antigenic determinant," *Mol. Immunol.* 23:709–715.

Geysen et al. (1987) *J. Immun. Meth.* 102:259–274.

Haag (2000) "Chemspeed Ltd.: Automated and unattended parallel synthesis integrating work–up and analysis," *Chimia* 54:163–164.

Haap et al. (1998) "FT–IR Mapping—A New Tool for Spatially–Resolved Characterization of Polymer–Bound Combinatorial Compound Libraries with Ir Microscopy," *Angew. Chem. Int. Ed.* 37(23):3311–3314.

Houghten (1985) "General method for the rapid solid–phase synthesis of large numbers of peptides," *Proc. Natl. Acad. Sci. USA* 82:5131–5135.

Houghten et al. (1991) "Generation and use of synthetic peptide combinatorial libraries for basic research and drug discovery" *Nature* 354:84–86.

Hu et al. (2000) "Automated solid–phase synthesis and photophysical properties of oligodeoxynucleotides labeled at 5'–aminothymidine with Ru(bpy)(2)(4–m–4'–cam–bpy)(2+)," *Inorg. Chem.* 39:2500–2504.

Hughes (1998) "Design of self–coded combinatorial libraries to facilitate direct analysis of ligands by mass spectrometry," *Med. Chem.* 41:3804–3811.

Keifer (1996) "Influence of resin structure, tether length, and solvent upon the high–resolution (1)H NMR spectra of solid–phase–synthesis resins," *J. Org. Chem.* 61:1558–1559.

Keifer et al. (2000) "Direct–injection NMR (DI–NMR): A flow NMR technique for the analysis of combinatorial chemistry libraries," *Journal of Combinatorial Chemistry* 2; 151–171.

Konings et al. (1996) "Deconvolution of combinatorial libraries for drug discovery: theoretical comparison of pooling strategies," *J. Med. Chem.* 39:2710–2719.

Lake et al. (2000) "Sample preparation for high throughput accurate mass analysis by matrix–assisted laser desorption/ionization time–of–flight mass spectrometry," *Rapid Commun. Mass Spectrom.* 14:1008–1013.

Lam et al. (1997) "The 'one–bead–one–compound' combinatorial library method," *Chem. Rev.* 97:411–448.

Lewis et al. (2000) "Automated high–throughput quantification of combinatorial arrays," *American Pharmaceutical Review* 3:63–68.

McGregor and Muskal (1999) "Pharmocophore fingerprinting 1. application to QSAR and focused library design," *J. Chem. Inf. Comput. Sci.* 39:569–574.

Meldal (1992) "PEGA: A flow stable polyethylene glycol dimethyl acryamide copolymer for solid phase synthesis," *Tetrahedron Lett.* 33:3077.

Metzger et al. (1993) "Ion–spray mass spectrometry and high–performance liquid chromatography. Mass spectrometry of synthetic peptide libraries," *Angew. Chem. Int. Ed.* 32:894–896.

Moran et al. (1995) *J. Am. Chem. Soc.* 117:10787–10788.

Newcomb et al. (1998) "Analysis of 9–fluorenylmethoxycarbonyl (Fmoc) loading of solid–phase synthesis resins by gas chromatography," *Biotech. Bioeng.* (Comb. Chem.) 61:55–60.

Nicolaou et al. (1995) *Angew. Chem. Int. Ed. Engl.* 34:24–2479.

North (2000) "Implementation of analytical technologies in a pharmaceutical development organization–looking into the next millennium," *Journal of Automated Methods and Management in Chemistry* 22:41–45.

Pickett et al. (1998) "Strategies for the design and comparison of combinatorial libraries using pharmacophoric descriptors," *J. Chem. Inf. Comput. Sci.* 38:144–150.

Pirrung et al., Pirrung (1997) "Spatially addressable combinatorial libraries," *Chem. Rev.* 97:473–488.

Schriemer et al. (1998) "Microscale Frontal Affinity–Chromatography with Mass–Spectrometric Detection—A New Method for the Screening of Compound Libraries," *Angew. Chem. Int. Ed.* 37(24):3383–3387.

Stevanovic and Jung (1993) "Multiple sequence analysis: Pool sequencing of synthetic and natural peptide libraries," *Anal. Biochem.* 212:212–220.

van Breemen et al. (1997) "Pulsed ultrafiltration mass spectrometry: A new method for screening combinatorial libraries," *Anal. Chem.* 69:2159–2164.

Wilson–Lingardo et al. (1996) "Deconvolution of combinatorial libraries for drug discovery: experimental comparison of pooling strategies," *J. Med. Chem.* 39:2720–2726.

Xiao and Nova (1997) *Comb. Chem.* 135–152.

Xiao et al. (1997) *Angew. Chem. Int. Ed. Engl.* 36:780–782.

Youngquist et al. (1994) "Matrix–assisted desorption ionization for rapid determination of the sequences of biologically active peptides isolated from support–bound combinatorial peptide libraries," *Rapid Commun. Mass Spectrom.* 8:77–81.

Zuckermann et al. (1992) "Design, construction and application of a fully automated equimolar peptide mixture synthesizer," *Int. J. Peptide Prot. Res.* 40:497–506.

Cargill and Maiefski (1996) "Automated combinatorial chemistry on solid phase," *Lab. Robotics. Automation* 8:139–148.

Castelino et al. (2000) "Automated sample storage for drug discovery," *Chim. Oggi.* 17:32–35.

Furka and Bennett (1999) "Combinatorial libraries by portioning and mixing," *Comb. Chem. High Throughput Screening* 2:105–122.

Groger et al. (2000) "1,3,5–Triazines, versatile industrial building blocks: Synthetic approaches and applications," *Chim. Oggi.* 18:12–16.

Terret, N., *Combinatorial Chemistry*, Oxford University Press (1998), pp. 7–32.

Merrifield (1985) "Solid phase Synthesis (Nobel Lecture)," *Angew. Chem. Int. Ed.* 32:894–896.

A1 segregate solid phase synthesis units into $n$ separate first stage reaction vessels to provide $m*f$ solid phase synthesis units in each of the $n$ vessels

A2 deliver different first components to each of the $n$ separate first stage reaction vessels to yield first stage reacted solid phase members following reaction of the different first components with the solid phase synthesis units

A3 segregate the first stage reacted solid phase members from the $n$ separate first stage reaction vessels into $m$ separate second stage reaction vessels by distributing at least one of the first stage reacted solid phase members from each of the separate first stage reaction vessels into each second stage reaction vessel

A4 deliver different second components to the second stage reaction vessels to yield the combinatorial library following reaction of the different second components with the first stage reacted solid phase members

A5 detect distinguishing physical properties of selected members of the combinatorial library

Fig. 4A

B1 segregate the at least $n*m*f$ solid phase synthesis units into $p$ separate third stage reaction vessels such that each separate third stage reaction vessel includes at least n*m*f /p solid phase synthesis units

B2 deliver different third components to each of the separate third stage reaction vessels to yield third stage reacted solid phase members following reaction of the different third components with the solid phase synthesis units

B3 combine and mix the third stage reacted solid phase members in a single pool to provide the solid phase synthesis units for A1

Fig. 4B

NONREDUNDANT SPLIT/POOL SYNTHESIS OF COMBINATORIAL LIBRARIES

CROSS-REFERENCES TO RELATED APPLICATIONS

This application is related to U.S. Ser. No. 60/180,111, entitled "NONREDUNDANT SPLIT POOL SYNTHESIS OF COMBINATORIAL LIBRARIES," by Sepetov et al., filed Feb. 3, 2000; U.S. Ser. No. 60/180,115 entitled "STRUCTURE DETERMINATION METHODS USING MASS MEASUREMENT," by Sepetov et al., filed Feb. 3, 2000; U.S. Ser. No. 60/180,112 entitled "SYNTHETIC METHODS TO CREATE A SHARED CHEMICAL HISTORY," by Sepetov et al., filed Feb. 3, 2000; and U.S. Ser. No. 60/188,937 entitled "NEW SYNTHETIC METHODS TO CREATE A SHARED CHEMICAL HISTORY," by Sepetov et al., filed Mar. 10, 2000, each of which are incorporated herein by reference in their entirety, for all purposes. The present application claims priority to and the benefit of these related applications pursuant to 35 U.S.C. §119(e), as well as any other applicable statute or rule.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Modern methods of identifying compounds having desired chemical or physical properties typically involve assembling libraries of compounds, which are then systematically screened for members with the desired properties. One method of assembling compound libraries involves the highly labor-intensive process of isolating and characterizing naturally occurring compounds. Another approach involves synthesizing libraries of compounds using combinatorial processes in which sets of compounds are prepared from sets of building blocks via multi-step synthesis. The libraries produced by the latter approach typically successfully emulate the structural characteristics of naturally occurring compounds. In addition, combinatorial libraries also generally provide more rapid access to larger collections of more diverse compounds that may incorporate optimized chemical or physical properties into their structures.

Numerous techniques have been devised for producing combinatorial libraries. Many of these techniques utilize solid supports to exploit efficient "split-and-pool," or simply "split/pool," synthesis methods to assemble all possible combinations of a set of building blocks. The split/pool method typically utilizes a pool of solid supports containing reactive moieties. This pool is initially split into a number of individual pools of solid supports. Each pool is then subjected to a first reaction or randomization that results in a different modification to the solid supports in each of the pools. After the reaction, the pools of solid supports are combined, mixed, and split again. Each split pool is subjected to a second reaction or randomization that again is different for each of the pools. The process is continued until a library of target compounds is formed. Split/pool synthesis is a very efficient method that allows synthesis of a library of $n1 \times n2 \times n3$ members with just $n1+n2+n3$ reactions. Split/pool combinatorial synthesis is described further in, e.g., Furka and Bennett (1999) "Combinatorial libraries by portioning and mixing," Comb. Chem. High Throughput Screening 2:105–122 and Lam et al. (1997) "The 'one-bead-one-compound' combinatorial library method," Chem. Rev. 97:411–448.

The relative simplicity of split/pool synthesis is achieved at the expense of losing information about the identity of individual compounds during synthesis. As a consequence, structural determinations of synthesized compounds are typically performed following synthesis. Two general categories of techniques have been developed to identify the structures of individual library members during mixture deconvolution, namely, coding and noncoding strategies. Coding methods provide structure determination for libraries through the reading of a code that represents unambiguously the series of steps that a given solid support was subjected to during synthesis. The coding entity may be chemical which relies on the iterative coupling of chemical tags (e.g., peptides, oligonucleotides, isotopes, binary molecule systems, or the like) to orthogonally functionalized beads during library synthesis, where the tag structure is read using various analytical techniques. See, e.g., Czarnik (1997) "Encoding methods for combinatorial chemistry," Curr. Opin. Chem. Biol. 1:60–66 and Barnes et al. (1998) S. Rec. Res. Dev. Org. Chem. 2:367–379. Various nonchemical encoding techniques have also been developed which record the synthetic or chemical history of library members by physical methods. See generally, Xiao and Nova (1997) Comb. Chem. 135–152. These techniques include, e.g., radiofrequency encoding (see, e.g., Nicolaou et al. (1995) Angew. Chem. Int. Ed. Engl. 34:24–2479 and Moran et al. (1995) J. Am. Chem. Soc. 117:10787–10788), and optical or color encoding (see, e.g., Xiao et al. (1997) Angew. Chem. Int. Ed. Engl. 36:780–782), where solid-phase supports are encapsulated in an encoded porous container.

Noncoding methods of determining compound structure involve techniques which do not utilize additional encoding constructs associated with library members structures. These methods include, e.g., synthesis in a fixed array (parallel synthesis), where a compound's position within the array identifies the series of synthetic steps used to create the compound; direct deconvolution by pooling methods, where deconvolution of active structure is performed through selection of active pools from various synthetic cycles; and direct deconvolution by bioanalytical methods, where the chemical structure of active library components is determined by bioanalytical methods. See, e.g., U.S. Pat. No. 5,143,854 "LARGE SCALE PHOTOLITHOGRAPHIC SOLID PHASE SYNTHESIS OF POLYPEPTIDES AND RECEPTOR BINDING SCREENING THEREOF," issued Sep. 1, 1992 to Pirrung et al., Pirrung (1997) "Spatially addressable combinatorial libraries," Chem. Rev. 97:473–488, DeWitt et al. (1993) "'Diversomers': an approach to nonpeptide, nonoligomeric chemical diversity," Proc. Natl. Acad. Sci. USA 90:6909–6913, Geysen et al. (1986) "A priori delineation of a peptide which mimics a discontinuous antigenic determinant," Mol. Immunol. 23:709–715, and Geysen et al. (1987) J. Immun. Meth. 102:259–274 (parallel synthesis of peptides on rods or pins).

Both coding and noncoding approaches to determining the identity of structures following split/pool synthesis have significant disadvantages. Although encoding strategies allow the use of the most efficient form of split/pool synthesis, pooling of solid phase synthesis units during intermediate steps in synthesis, encoding inevitably records only the series of steps that the support was exposed to during synthesis, which should, but does not necessarily, lead to the desired products. Furthermore additional steps are often required during synthesis and decoding to assign structure accurately. Parallel synthesis does not allow the most efficient means of synthesis as, by design, the support is split and not pooled during synthesis in order to unambiguously predict a structure to be present at a location in an array of compounds. Finally, the time and labor intensive nature of the processes employed to decode the synthetic product limit the application of this method to a small portion of the total number of synthetic products—typically, those structures which show activity in high throughput screening assays. In this approach, valuable information about closely related but inactive structures is not obtained.

Combinatorial chemistry has advanced to the point that it is not enough to synthesize a desired set of compounds. It has now become equally important to consider the steps that immediately follow synthesis. For example, within the last several years there is a clear trend in combinatorial chemistry towards producing pure, characterized individual compounds. Consequently, compound analysis, to assess purity and confirm that the intended compounds were synthesized, is routinely conducted following synthesis of combinatorial libraries. Mass spectrometry (MS) is usually the method used for confirmation of structure. High performance liquid chromatography (HPLC) is most often used for purity assessment. Typically, components of a combinatorial library are subjected to HPLC/MS analysis for quality control which is independent of the way in which the relevant library was synthesized (by parallel synthesis, encoding, etc). Also, the format of the screening assays, which will be used for testing compounds originating from combinatorial synthesis, is relevant.

From the above, it is apparent that there is a substantial need for new methods which permit more efficient production of large libraries of compounds with easily identifiable structures by combinatorial synthesis and that enable all steps, including synthesis, analysis, and screening, to be performed as efficiently as possible. The present invention provides new methods, and related systems, for efficiently synthesizing and identifying structural features of combinatorial library members. These and a variety of additional features will become evident upon complete review of the following.

SUMMARY OF THE INVENTION

The present invention provides a method of identifying selected members of a synthesized library of materials, which in several embodiments is completely or partially computer implemented. The methods relate to synthetic strategies which use synthetic pooling strategies and, e.g., data analysis which accounts for shared chemical histories of products of the synthetic strategies, to determine unambiguously the structures of the synthesized products.

The methods typically include, e.g., (a) providing at least $n*m*f$ solid phase synthesis units in which n is equal to a number of choices of different first components in a first stage of synthesis, m is equal to a number of choices of different second components in a second stage of the synthesis, and f is equal to a number of solid phase synthesis units to include identical materials upon completion of the synthesis. The method also typically includes (b) segregating the solid phase synthesis units into n separate first stage reaction vessels in which each separate first stage reaction vessel comprises at least $m*f$ solid phase synthesis units and (c) reacting the solid phase synthesis units in each of the separate first stage reaction vessels with a different first component in the first stage of the synthesis. Thereafter, the method typically includes (d) segregating the solid phase synthesis units of (c) into m separate second stage reaction vessels by distributing at least one of the solid phase synthesis units from each of the separate first stage vessels into each separate second stage reaction vessel such that each of the separate second stage reaction vessels comprises at least $n*f$ solid phase synthesis units and (e) reacting the solid phase synthesis units in each of the separate second stage reaction vessels with a different second component in the second stage of the synthesis to synthesize the library of the materials (e.g., producing a combinatorial chemical library or the like). The method additionally includes (f) detecting one or more distinguishing physical properties (e.g., different molecular masses or the like) of selected members of the library and (g) identifying the selected members based on the one or more detected distinguishing physical properties. Data deconvolution which takes advantage of an understanding of the shared chemical histories of the various solid phase supports during synthesis can be used to assign structures to the various library members based upon the distinguishing physical property or properties.

In some embodiments, the at least $n*m*f$ solid phase synthesis units are subjected to one or more split/pool synthesis steps prior to (a). Thus, (a) optionally includes (i) segregating the at least $n*m*f$ solid phase synthesis units into p separate third stage reaction vessels in which p is equal to a number of choices of different third components in a third stage of the synthesis, and in which each separate third stage reaction vessel comprises at least $n*m*f/p$ solid phase synthesis units. In certain embodiments, the at least $n*m*f$ solid phase synthesis units include $n*m*f*p$ solid phase synthesis units. In this embodiment, (a) also optionally includes (ii) reacting the solid phase synthesis units in each of the separate third stage reaction vessels with a different third component in the third stage of the synthesis and (iii) combining and mixing the solid phase synthesis units of (ii) in a single pool to provide the at least $n*m*f$ solid phase synthesis units. Optionally, this embodiment further includes (iv) separating the at least $n*m*f$ solid phase synthesis units of (iii) into $n*m$ separate containers in which the $n*m$ separate containers are segregated into the n separate first stage reaction vessels as the solid phase synthesis units of (b). As an additional option, this embodiment further includes separating the at least $n*m*f$ solid phase synthesis units of (c) into $n*m$ separate containers in which the $n*m$ separate containers are segregated into the m separate second stage reaction vessels as the solid phase synthesis units of (d).

In certain embodiments, (f) further comprises cleaving the materials from the solid phase synthesis units prior to detecting the one or more distinguishing physical properties (e.g., different molecular masses or the like). In other embodiments, the solid phase synthesis units of (e) each include multiple particles combined together, and (f) further includes separating selected particles from other particles and cleaving synthesized materials from the selected particles prior to detecting the one or more distinguishing physical properties. The different molecular masses are detected, most typically, by mass spectrometry. In certain embodiments, structural identification of the selected members includes subtracting a mass of the different second component reacted in a particular separate second reaction vessel from the different detected masses of the selected members to determine masses of different first components included in each of the selected members. The structural identification typically accounts for mass defects of reaction of the selected members. Optionally, structural identification of the selected members includes determining a fingerprint of library members in one or more of the separate second stage reaction vessels.

In preferred embodiments, structural identification of the selected members includes correlating the different detected masses of the selected members to a physical or logical matrix that includes masses for each individual library member. The correlation is generally computer implemented. For example, at least one entry in the matrix includes a summation of masses of different combinations of first and second components. Some or all entries in the matrix can be summations of different combinations of first and second components, and optionally, of other components (e.g., third components or the like). Furthermore, correlations of the different detected masses to entries in the matrix typically account for mass defects of reaction of the selected members (mass differences between predicted and observed masses).

The present invention also relates to a combinatorial library synthesis system that includes (a) a plurality of reaction vessels, (b) a handling system (including, e.g., a bead handler or the like) configured to move solid phase synthesis units and reagents to and from the plurality of reaction vessels, (c) a detection system (e.g., a mass spectrometer or the like) to detect one or more distinguishing physical properties (e.g., different masses or the like) of selected members of the combinatorial library, and (d) a computer operably connected to the handling and detection systems. The computer can include system software which directs the handling or detection systems to: (i) segregate the solid phase synthesis units into n separate first stage reaction vessels to provide m*f solid phase synthesis units in each of the n vessels in which n is equal to a number of choices of different first components in a first stage of a library synthesis, m is equal to a number of choices of different second components in a second stage of the library synthesis, and f is equal to a number of solid phase synthesis units which comprise identical materials on completion of the library synthesis. The system software can also direct the handling or detection systems to: (ii) deliver one or more of the different first components to each of the n separate first stage reaction vessels to provide for reaction of the different first components with the solid phase synthesis units to provide first stage reacted solid phase members and (iii) segregate the first stage reacted solid phase members from the n separate first stage reaction vessels into m separate second stage reaction vessels by distributing at least one of the first stage reacted solid phase members from each of the separate first stage reaction vessels into each second stage reaction vessels such that each second stage reaction vessel comprises at least n*f solid phase synthesis units. Separately or in addition, the system software can also direct the handling or detection systems to: (iv) deliver one or more different second components to the second stage reaction vessels to provide for reaction of the different second components with the first stage reacted solid phase members to provide the combinatorial library and (iv) detect one or more distinguishing physical properties (e.g., different masses or the like) of the selected members of the combinatorial library. The system software also typically directs the handling system in (iv) to effect cleavage of combinatorial library members from the solid phase synthesis units.

In some embodiments prior to (i), the system software directs the handling system to: (1) segregate at least n*m*f solid phase synthesis units into p separate third stage reaction vessels in which p is equal to a number of choices of different third components in a third stage of the library synthesis, and in which each separate third stage reaction vessel comprises the at least n*m*f/p solid phase synthesis units and (2) deliver one or more of the different third components to each of the separate third stage reaction vessels to provide for reaction of the different third components with the solid phase synthesis units to provide third stage reacted solid phase members, and (3) combine and mix the third stage reacted solid phase members in a single pool to provide the solid phase synthesis units for (i). In some embodiments, the system software further directs the handling system to: (4) separate the solid phase synthesis units of (3) into n*m separate containers in which the n*m separate containers are segregated into the n separate first stage reaction vessels as the solid phase synthesis units of (i). Optionally, the system software further directs the handling system to separate the solid phase synthesis units of (3) into n*m separate containers in which the n*m separate containers are segregated into the m separate second stage reaction vessels as the solid phase synthesis units of (iii). As an additional option, each of the n*m separate containers comprises multiple particles combined together.

In preferred embodiments, the computer further includes at least one database having a logical matrix corresponding to masses of members of a virtual library that are correlated with the detected masses of the combinatorial library members produced by the system to thereby identify chemical structures of the combinatorial library members. Correlations typically account for mass defects of reaction. At least one entry in the logical matrix typically includes a summation of masses of different combinations of first and second components.

The invention can also be embodied in kits, e.g., including any of the system elements for performing any of the methods herein, and optionally further including containers for holding any of the relevant system elements, packaging materials, instructional materials for practicing the method, and the like.

BRIEF DESCRIPTION OF THE DRAWING

FIG. 4A schematically illustrates steps performed by the handling and detection systems under the control of system software in one embodiment of the invention. FIG. 4B schematically illustrates additional steps (i.e., additional to those schematically illustrated in FIG. 4A) performed by the handling system under the control of system software in another embodiment of the invention.

DEFINITIONS

Figure 1:
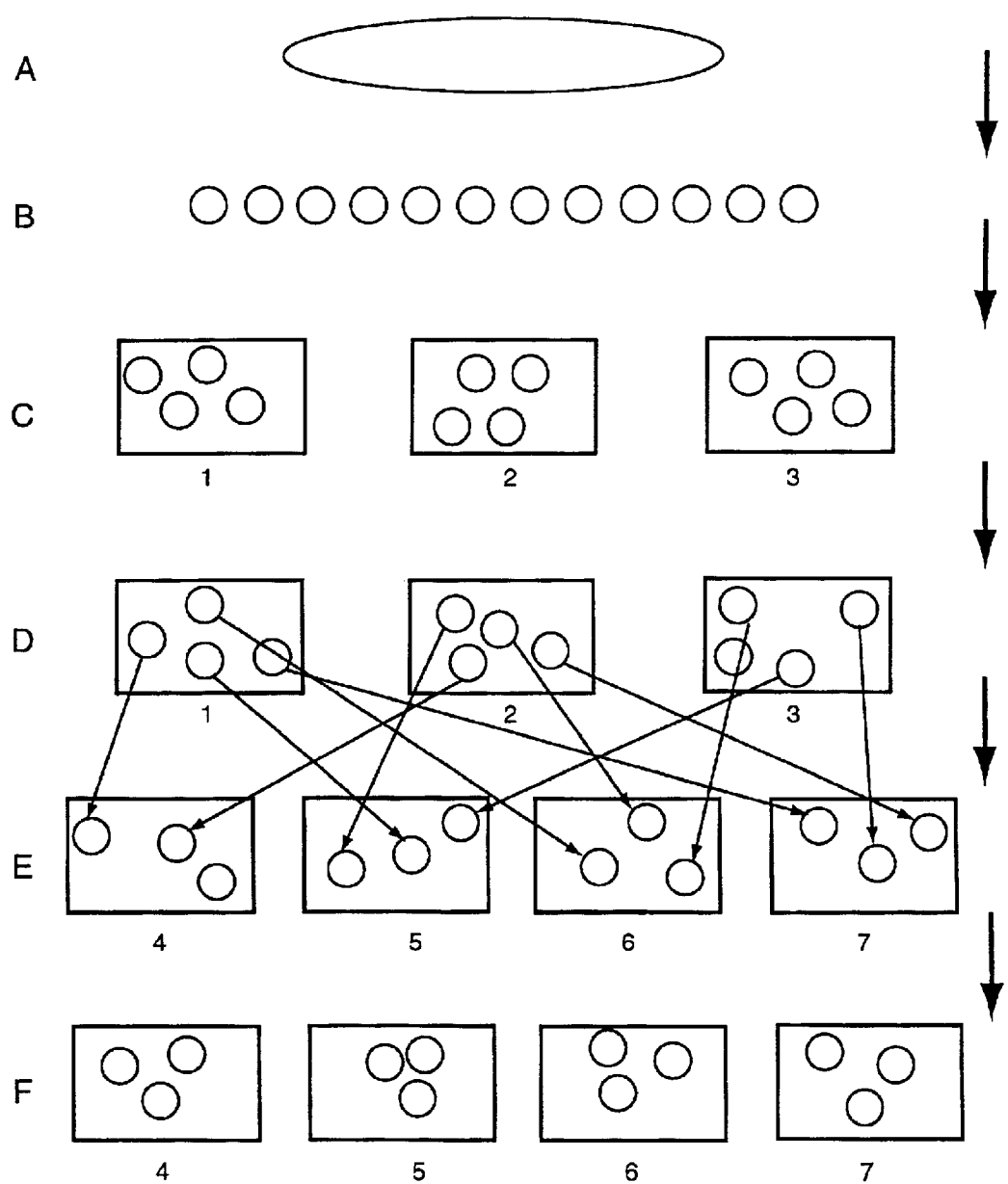
FIG. 1 schematically illustrates a nonredundant split/pool synthesis method.

Unless otherwise indicated, the following definitions supplement those in the art.

A "library" refers to a set of compounds or materials. A "combinatorial" library refers to a set of compounds or materials prepared by combinatorial chemistry. A library optionally includes a collection of pools or sub-libraries. A "sub-library" means a sub-set of compounds or materials, e.g., a collection of materials or compounds obtained from solid phase synthesis units, e.g., within a particular container or vessel in the methods described herein. A library "member" refers, e.g., to a specific material or compound that is included in a library, or an uncharacterized physical product or material of a library synthesis. A "virtual" library refers to a representation of a physical library, such as a representation of the library in electronic or paper form. Members of a virtual library are optionally represented in essentially any physical or logical matrix. The building blocks utilized for such a library may or may not exist, and the chemical steps to form such a library may or may not have been tested. These virtual libraries are optionally used in the design and evaluation of possible physical/chemical libraries. See, also, e.g., Sheridan and Kearsley (1995) "Using a genetic algorithm to suggest combinatorial libraries," *J. Chem. Inf. Comput. Sci.* 35:310–320.

A "resin" refers to an insoluble material (e.g., a polymeric material) or particle which allows ready separation from liquid phase materials by filtration. Resins can be used to carry library members (e.g., solid supports) or reagents, or to trap excess reagents or reaction by-products, or the like. A "solid support" refers to an insoluble, functionalized, polymeric material or particle to which library members or reagents may be attached (e.g., via a linker) allowing them to be readily separated (by filtration, centrifugation, etc.) from excess reagents, soluble reaction by-products or solvents. Examples of solid supports suitable for the methods described herein include, e.g., glass supports, plastic supports, silicon supports, chips, beads, pins, filters, membranes, microwell plates, slides, or the like. See also, Sherrington (1998) "Preparation, structure, and morphology of polymer supports," *Chem. Commun.* 2275–2286, Winter "Supports for solid-phase organic synthesis," In *Combinatorial Peptide and Non-Peptide Libraries* (G. Jung, ed.), pp. 465–509. VCH, Weinheim (1996), and Hudson (1999) "Matrix-assisted synthetic transformations: a mosaic of different contributions. 1. The pattern emerges," *J. Comb. Chem.* 1:330–360. A solid support is "functionalized" when it includes a linker, a scaffold, a building block, or other reactive moiety attached thereto, whereas a solid support is "nonfunctionalized" when it lack such a reactive moiety attached thereto.

A "solid phase synthesis unit" refers to a certain amount of material upon or in which a combinatorial synthesis is performed. Solid phase synthesis units optionally include, e.g., single particles of solid supports or resins such as beads, crowns, pieces of polymer, pieces of cellulose (paper, cotton, etc.), or the like. Solid phase synthesis units also optionally include, e.g., multiple particles combined together, e.g., which are not separated during combinatorial synthesis, such as a tea-bag or other porous container with beads, an array of solid supports, or the like. Containers such as tea-bags are discussed further in, e.g., Houghten (1985) "General method for the rapid solid-phase synthesis of large numbers of peptides," *Proc. Natl. Acad. Sci. USA* 82:5131–5135 and in U.S. Pat. No. 4,631,211 "MEANS FOR SEQUENTIAL SOLID PHASE ORGANIC SYNTHESIS AND METHODS USING THE SAME," issued Dec. 23, 1986 to Houghten. A "container" refers to a physical grouping of multiple solid phase supports. A "reaction vessel" refers to a vessel capable of containing solid phase synthesis units, whether present as single particles of solid supports or resins, or as multiple particles combined together in, e.g., a container. One type of reaction vessel is a "microwell plate," which is a substrate that includes a plurality of regions that retain one or more fluidic materials.

A "choice" refers to the alternative variables (e.g., combination of various different components or building blocks, etc.) for a given stage in a combinatorial synthesis. The term "stage" refers to a step in a sequential combinatorial synthesis of a compound or material.

A "building block" or "component" refers to one of a number of interchangeable reagents which are optionally used in combinatorial library synthesis, at least part of the structure of which becomes incorporated into an intermediate or final product. Building blocks or components may include a set of reagents that introduces diversity into library products and/or one that results in an identical conversion for each member of the library. A "scaffold" or "template" refers to a core portion of a molecule common to all members of a combinatorial library or sub-library.

A "linker" or "tether" refers to a bifunctional chemical moiety attaching a compound to, e.g., a solid support which can be cleaved to release materials or compounds from the support. A careful choice of linker allows cleavage to be performed under appropriate conditions compatible with the stability of the compound and assay method. Additional description of linker molecules is provided in, e.g., Backes and Ellman (1997) "Solid support linker strategies," *Curr. Opin. Chem. Biol.* 1:86–93, Backes et al. (1996) "Activation method to prepare a highly reactive acylsulfonamide "safety-catch" linker for solid-phase synthesis," *J. Amer. Chem. Soc.* 118:3055–3056, Backes and Ellman (1994) "Carbon-carbon bond-forming methods on solid support. Utilization of Kenner's "Safety-Catch" linker," *J. Amer. Chem. Soc.* 116:11171–11172, Hoffmann and Frank (1994) "A new safety-catch peptide-resin linkage for the direct release of peptides into aqueous buffers," *Tetrahedron Lett.* 35:7763–7766, Kocis et al. (1993) "Symmetrical structure allowing the selective multiple release of a defined quantity of peptide from a single bead of polymeric support," *Tetrahedron Lett.* 34:7251–7252, and Plunkett and Ellman (1995) "A silicon-based linker for traceless solid-phase synthesis," *J. Org. Chem.* 60:6006–6007.

The term "cleavage" refers to a process of releasing a material or compound from a solid support, e.g., to permit analysis of the compound by solution-phase methods. See, e.g., Wells et al. (1998) "Cleavage and Analysis of Material from Single Resin Beads," *J. Org. Chem.* 63:6430–6431.

A "set" includes a group or a collection of at least two solid phase synthesis units, virtual or actual masses, components, synthesis products, particles, or other materials.

"Deconvolution" refers to a process of rendering, e.g., a combinatorial library less complex and/or of identifying or characterizing one or more members of the library. The process optionally includes identifying the structure of a particular library member. Optionally, the process includes optimizing an activity of interest by, e.g., fractionating (e.g., by resynthesis, or by elaborating a partial library) a pool with some level of the desired activity to give a set of smaller pools. Repetition of this strategy (i.e., "iterative deconvolution") ideally leads to single members with a high level of activity. Additional details regarding combinatorial library deconvolution are described in, e.g., Houghten et al. (1991) "Generation and use of synthetic peptide combinatorial libraries for basic research and drug discovery" *Nature*

354:84–86, Konings et al. (1996) "Deconvolution of combinatorial libraries for drug discovery: theoretical comparison of pooling strategies," *J. Med. Chem.* 39:2710–2719, and Wilson-Lingardo et al. (1996) "Deconvolution of combinatorial libraries for drug discovery: experimental comparison of pooling strategies," *J. Med. Chem.* 39:2720–2726.

A "mass defect of reaction" is a portion or deficiency of a detected mass of a given library member that is not attributable to the predicted chemical structure of the member alone. For example, a mass defect of reaction may be due to one or more water or other molecules that are, e.g., electrostatically associated with the library member. In addition, library members that experienced conditions that should have produced a common chemical transformation and change in molecular weight for all compounds in the group (i.e., library members with a shared chemical history), may have identical, different, or no mass defects of reaction.

The phrase "structural identification" refers to the identification of all, or a constituent part (e.g., a substituent or functional group) of a compound's chemical or physical structure.

A "fingerprint" refers to a representation of a compound or library that describes a set of attributes (descriptors), such as atom connectives, 3-D structure or physical properties. For example, the representation can be a numerical representation, an image (e.g., a barcode), or the like. See, also, e.g., Pickett et al. (1998) "Strategies for the design and comparison of combinatorial libraries using pharmacophoric descriptors," *J. Chem. Inf. Comput. Sci.* 38:144–150 and McGregor and Muskal (1999) "Pharmocophore fingerprinting 1. application to QSAR and focused library design," *J. Chem. Inf. Comput. Sci.* 39:569–574. A "descriptor" refers to a numerical representation of a molecular property, including, e.g., bulk properties (e.g., log P, molecular weight or mass), two-dimensional (2-D) features (atom connectivities) or three-dimensional (3-D) features (molecular shape). A fingerprint comprises a set of descriptors.

DETAILED DISCUSSION OF THE INVENTION

Introduction

The present invention generally relates to the combinatorial synthesis of large numbers of compounds. In particular, the invention provides a method for generating combinatorial libraries on solid phase synthesis units in which each of a set of predetermined species of test or combinatorial compounds (e.g., systematic variants of a chemical structure) is present on a predetermined number of solid phase synthesis units (e.g., individual solid supports, or collections of solid supports in a container, array, or the like), preferably on only one, with each solid phase synthesis unit having only a single species of combinatorial compound is provided. Each of the predetermined species of combinatorial compounds is prepared with relative certainty because the method does not employ a random division of the solid phase synthesis units.

The method does not require tracking or encoding strategy of individual solid phase synthesis units during synthesis. The identity of each of the combinatorial compounds is determined following synthesis based on distinguishing physical properties of the combinatorial compounds which are measured during a quality control procedure, and using knowledge of the shared chemical history of the combinatorial compounds (e.g., derived from information about the container from which the compounds originated and, thus, the relevant reactions to which the solid supports were exposed). Information about the chemical history of a container may be obtained, e.g., by analysis of multiple solid phase particles from the container. Additional discussion of solid phase synthesis is provided in, e.g., Bunin et al. (1994) "The combinatorial synthesis and chemical and biological evaluation of 1,4-benzodiazepine library," *Proc. Natl. Acad. Sci. USA* 91:4708–4712, Bunin and Ellman (1992) "A general and expedient method for the solid phase synthesis of 1,4-benzodiazepine derivatives," *J. Amer. Chem. Soc.* 114:10997–10998, Meldal (1992) "PEGA: A flow stable polyethylene glycol dimethyl acryamide copolymer for solid phase synthesis," *Tetrahedron Lett.* 33:3077, and Merrifield (1985) "Solid phase synthesis (Nobel lecture)," *Angew. Chem.* 97:801. See, also, Seneci, *Solid Phase Synthesis and Combinatorial Technologies*, John Wiley & Sons, (2000), Burgess (Ed) *Solid-Phase Organic Synthesis*, John Wiley & Sons, (2000), and Kates and Albercio (Eds) *Solid-Phase Synthesis: A Practical Guide*, Marcel Dekker, (2000).

The invention additionally provides embodiments of the method that generate combinatorial libraries in which containers with a random mixture of solid phase particles are divided and combined together in a non-random manner without exchange of particles between containers. The method is intended to provide, e.g., combinatorial compounds with more than two points of chemical diversity. The invention also includes automated systems and kits for performing the synthetic and structural identification methods.

Nonredundant Split Pool Synthesis

The present invention provides a method of identifying selected members of a synthesized library of materials. In preferred embodiments, the method is completely or partially computer implemented. These aspects are described further below with regard to combinatorial library synthesis systems. The method generally includes (a) providing at least $n*m*f$ solid phase synthesis units in which n is equal to a number of choices of different first components in a first stage of synthesis, m is equal to a number of choices of different second components in a second stage of the synthesis, and f is equal to a number of solid phase synthesis units to include identical materials upon completion of the synthesis. In one class of embodiments, f is equal to one. Solid phase synthesis units are typically functionalized either by a linker for attaching reactants in the first randomization to the solid phase or by certain molecular structures which may be considered as the first point of diversity for combinatorial compounds. Optionally, one or more of the solid phase synthesis units include single functionalized particles or single non-functionalized particles (e.g., a controls or the like). As a further option, at least two of the solid phase synthesis units include single particles having different functionalities attached thereto. In certain embodiments, at least one of the separate first stage reaction vessels includes at least two solid phase synthesis units comprising different functionalities.

The method also includes (b) segregating the solid phase synthesis units into n separate first stage reaction vessels (e.g., flasks, wells of a microwell plate, or the like) in which each separate first stage reaction vessel comprises at least $m*f$ solid phase synthesis units and (c) reacting the solid phase synthesis units in each of the separate first stage reaction vessels with a different first component in the first stage of the synthesis. For example, appropriate reagents are typically added to each reaction vessel to process them in stages. In certain embodiments, each separate first stage reaction vessel in (b) includes $m*f$ solid phase synthesis units. As a further option, at least one of the separate first stage reaction vessels optionally includes at least two solid phase synthesis units having different functionalities attached thereto. Thereafter, the method includes (d) segregating the solid phase synthesis units of (c) into m separate second stage reaction vessels by distributing at least one of the solid phase synthesis units from each of the separate first stage vessels into each separate second stage reaction vessel such that each of the separate second stage reaction vessels comprises at least n*f solid phase synthesis units and (e) reacting the solid phase synthesis units in each of the separate second stage reaction vessels with a different second component in the second stage of the synthesis to synthesize the library of the materials (e.g., a combinatorial chemical library or the like). Distribution is typically performed in a way that each group of supports used in the first stage of synthesis will be divided in m subgroups, and new groups will be created by combining together single subgroups of supports from each group used in the first stage.

In certain embodiments, each of the separate second stage reaction vessels in (d) comprises n*f solid phase synthesis units. Optionally, the solid phase synthesis units of (d) are randomly or non-randomly arranged in at least one of the second stage reaction vessels. Each different first and second component typically independently includes an organic or an inorganic component. The method additionally includes (f) detecting one or more distinguishing physical properties (e.g., different masses or the like) of selected members of the library and (g) identifying the selected members based on the one or more detected distinguishing physical properties.

In alternative embodiments, distribution of solid phase synthesis units from n groups in the first stage of synthesis to m groups, which will be used in the second stage of synthesis may be performed by using two-dimensional arraying. With this technique, supports from each of n groups are arrayed in n columns (or rows) in a two-dimensional matrix. To create m new groups one combines all supports from any f rows (or columns) of the matrix in a group and repeats the process m times. For example, in some embodiments, (b) includes providing one or more of the at least m*f solid phase synthesis units in one or more two-dimensional arrays in the separate first stage reaction vessels, whereas in other embodiments, one or more of the at least m*f solid phase synthesis units in one or more of the separate first stage reaction vessels are non-arrayed. Similarly, in certain embodiments, (d) includes providing one or more of the at least n*f solid phase synthesis units in one or more two-dimensional arrays in the separate second stage reaction vessels, whereas in other embodiments, one or more of the at least n*f solid phase synthesis units in one or more of the separate second stage reaction vessels are non-arrayed.

FIG. 1 schematically illustrates a nonredundant split pool synthesis method which shows synthesis of a hypothetical library produced with two sets of building blocks (3 for the first randomization (R1) and 4 for the second randomization (R2)), with a total complexity of 3×4=12 compounds (i.e., n=3, m=4, and f=1). As shown, resin (depicted in A) is first split into 3×4=12 equal portions and distributed into 12 containers (depicted in B). For example, a suitable container is optionally a tea-bag or other porous container (e.g., any synthesis unit that is composed of inert porous compartments), or an array of the resin. As depicted in C, the containers are pooled in three reaction vessels (according to the number of R1 building blocks, i.e., n=3); thus, each reaction vessel holds four containers. Then, the coupling of the first set of building blocks is performed in each reaction vessel. As depicted in D, the containers are pooled in such a way that each new pool has one container from each of the pools (i.e., reaction vessels) used in C and D. As a result, four new pools are formed (according to the number of R2 building blocks, i.e., m=4) each holding three containers (depicted in E). An advantage of this method is that individual containers do not need to be tracked (e.g., labeled) during pooling. In this example, the only condition is that one container is taken from each pool in order to ensure that synthesis of all 3×4 compounds is accomplished.

Since containers are not tracked during synthesis, one more step is used for library member identification, namely, identification of the structure of compounds in each container. For example, the mass or molecular weight of a compound can be considered an internal code of a compound as long as there is no redundancy in molecular weights within a set of compounds. Accordingly, synthesis compounds within each vessel (4, 5, 6, 7; depicted in F) have the same R2 and every container has different R1 (see, scheme of pooling depicted in E). Thus, if the set of R1 includes building blocks with different molecular weights, measurement of the molecular weight of a compound from a container within every vessel with known R2 allows for unambiguous determination of R1 and consequently, to identification of the compound.

Typically, the identity of a compound is determined during the quality control step following library synthesis. For example, liquid chromatography/mass spectrometry (LC/MS) experiments with detection of UV absorption is optionally used for analysis of the quality of compounds produced by combinatorial synthesis. In this case the selection of reactants with different molecular weights for use in the first stage of synthesis allows for unambiguous identification of test compounds. Differentiation of test compounds may be facilitated by a comparison of the physical properties of compounds within one group. Compounds which were synthesized using reactants with identical molecular weights in the first stage of synthesis may be differentiated based on differences in chromatographic retention times, different UV absorption, or other quantifiable physical parameters.

Methods of Creating a Shared Chemical History

In carrying out the synthesis, one may initially begin with a number of solid phase synthesis units or particles, e.g., typically at least about 100, more typically at least about 500, and usually at least about 1000. As mentioned, the particles can be functionalized either by a linker for attaching reactants in the first randomization to the solid phase or by certain molecular structures which may be considered as the additional point of diversity for combinatorial compounds.

In one embodiment, particles are divided into as many reaction vessels as there are numbers of choices in the first stage of the relevant synthesis procedure. Appropriate reagents are then added to each reaction vessel to process them in stages. Once the reactions are complete, the solid phase particles are combined into a single pool, followed by the distribution of the resulting mixture into a number of containers. The number of containers equals n*m*f where n is the number of choices of reactants in the second stage of synthesis, m is the number of choices of reactants in the third stage, and f is a predetermined number of containers, which will have identical chemical history (preferentially f=1). The containers are then be divided into n groups containing m*f containers in each. Each group of n*f containers is placed in a separate reaction vessel.

Figure 2:
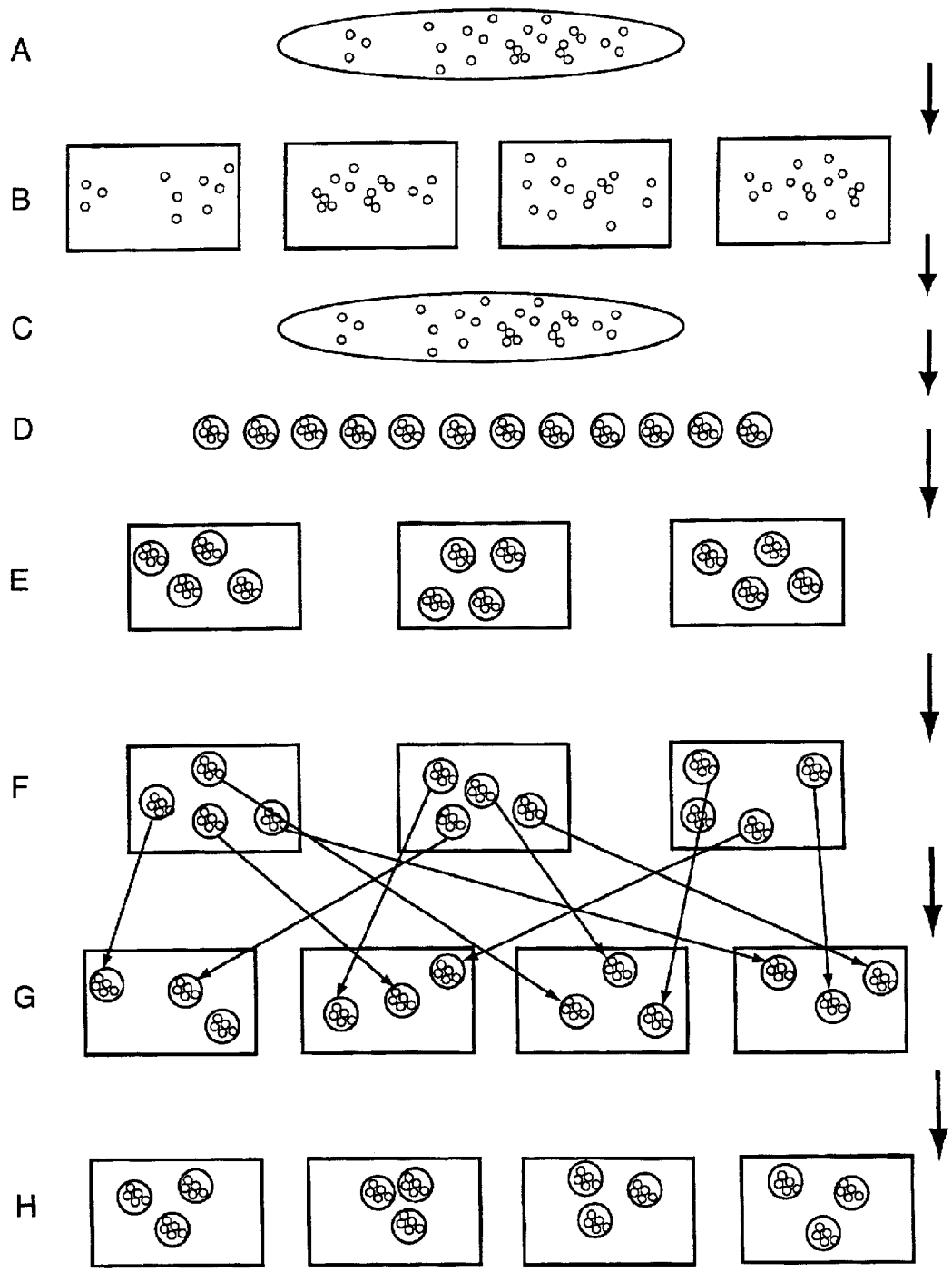
FIG. 2 schematically depicts an embodiment of the nonredundant split/pool synthesis method.

FIG. 2 schematically illustrates the synthesis of a hypothetical library produced with three sets of building blocks (4 for the first randomization (R1), 3 for the second randomization (R2), and four for the third randomization (R3)), with a total complexity of 4×3×4=48 compounds (i.e., n=3, m=4, p=4, and f=1). As shown, resin (depicted in A) is first split into four equal portions (i.e., p=4) and distributed into four reaction vessels, and reactions with first set of building blocks are performed (depicted in B). After reactions are complete, resin is pooled together and mixed (depicted in C). Then resin is divided into 3×4=12 equal portions and distributed into 12 containers (depicted in D). As mentioned, a suitable container optionally includes any synthesis unit that is composed of inert porous wells can be used. Containers are pooled in three reaction vessels (according to the number of R2 building blocks, i.e., n=3), thus each reaction vessel holds four containers (depicted in E). Then, the second set of building blocks is coupled in each respective reaction vessel. Thereafter, containers are pooled in such a way that each new pool has one container from each of the pools (vessels) used in E (depicted in F and G). As a result, four new pools are formed (according to the number of R3 building blocks, i.e., m=4) each holding three containers. Again, containers are not tracked during pooling—the only relevant condition is that one container is taken from each pool in order to ensure synthesis of all compounds. Finally, the third set of building blocks is added to the new pools (depicted in H) and synthesis of a library of 4×3×4 compounds is finished.

In another embodiment, solid phase synthesis units are divided into as many reaction vessels as there are numbers of choices in the first stage. Appropriate reagents are also added to each reaction vessel to process the first stage of synthesis. Once the reactions are complete, the solid phase particles are combined into a single pool, followed by the distribution of the resulting mixture into reaction vessels for the second stage of synthesis. Then, appropriate reagents are added to each reaction vessel to process the second stage of synthesis. Once the reaction(s) is complete, resins are distributed from each of n reaction vessels into m*f number of containers. The total number of containers equals n*m*f, where n is the number of choices of reactants in the second stage of synthesis, m is the number of choices of reactants in the third stage, and f is a predetermined number of containers that will have identical chemistry histories (preferentially f=1). The next step is reshuffling containers from existing n groups into m new groups containing m*f containers in each. Distribution is performed in such a way that each group of containers used in the second stage of synthesis will be divided in m subgroups. New groups will be created by combining together single subgroups of containers from each group used in the second stage. The new groups of containers are then placed in m reaction vessels and the third stage of synthesis is performed. Once the synthesis is complete, the library consists of n*m*f containers, each holding a mixture of solid phase particles with compounds that were synthesized with the same reactants in the second and in the third stage of synthesis but with different reactants in the first stage.

Figure 3:
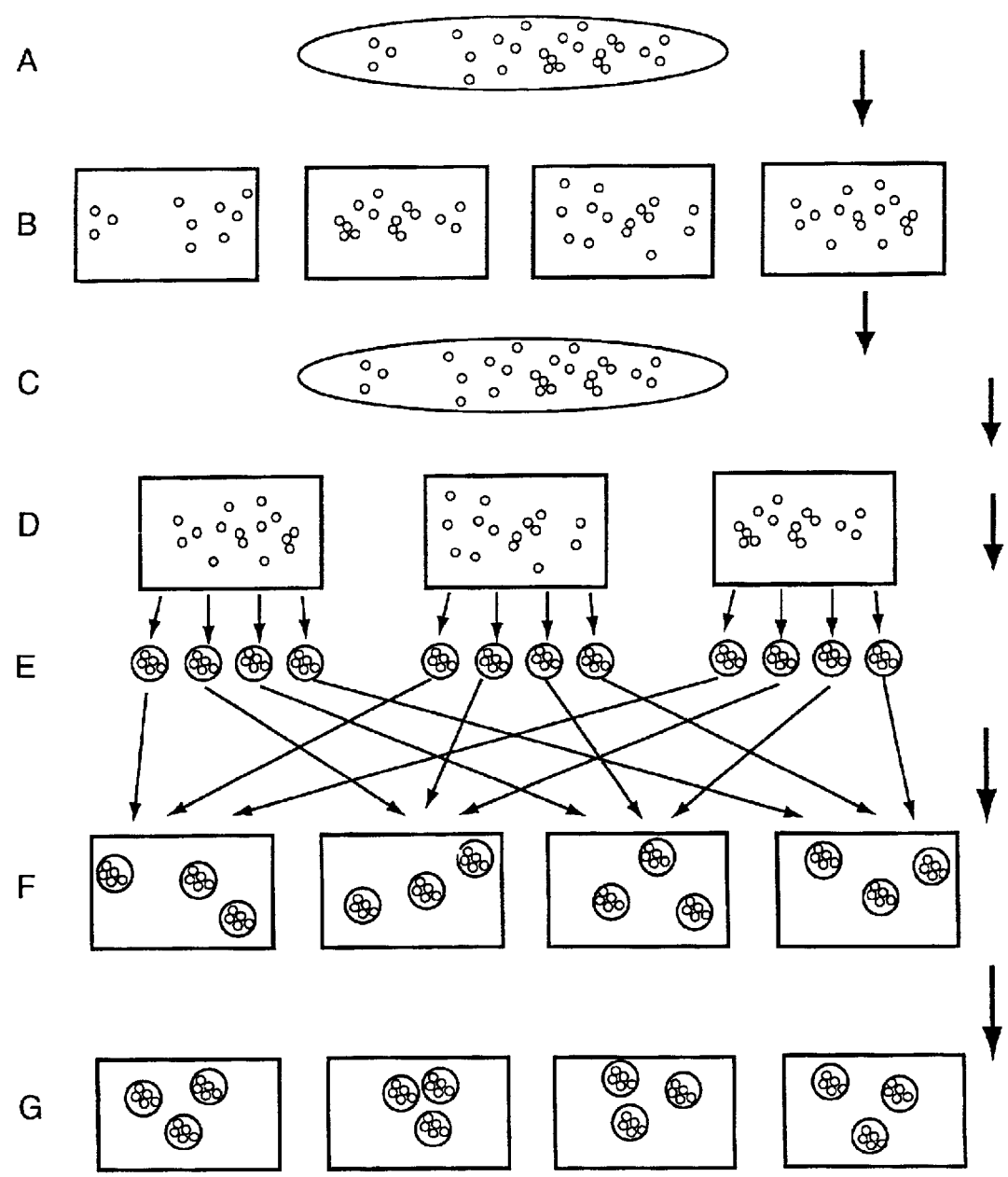
FIG. 3 schematically shows an embodiment of the nonredundant split/pool synthesis method.

FIG. 3 schematically illustrates distributions and redistributions of resin during synthesis of a hypothetical library produced with three sets of building blocks (4 for the first randomization (R1), three for the second randomization (R2), and four for the third randomization (R3)), with a total complexity of 4×3×4=48 compounds (i.e., n=3, m=4, p=4, and f=1). As shown, resin (depicted in A) is first split into four equal portions (i.e., p=4) and distributed into four reaction vessels, and reactions with first set of building blocks are performed (depicted in B). After reactions are complete, resin is pooled together and mixed (depicted in C). Then resin is then divided into three equal portions (i.e., n=3) and placed into reaction vessels for the second stage of the synthesis (depicted in D). Coupling of the second set of building blocks is performed in each reaction vessel correspondingly (depicted in D). Then, resin from each reaction vessel is distributed in three sets of four (i.e., m=4) containers, making 12 containers (depicted in E). As mentioned, any synthesis unit that is composed of inert porous walls can be used as a container. Thereafter, the containers are pooled in such a way that each reaction vessel for the third stage of synthesis has one container originating from each reaction vessel in the second stage of synthesis (depicted in F). Finally the third set of building blocks is added to the new pools (depicted in F) and synthesis of a library of 4×3×4 compounds is finished.

As mentioned, following library synthesis according to any of the methods described herein, physical properties of selected library members are optionally measured in liquid chromatography/mass spectrometry (LC/MS) experiments, which is one of the most frequently used methods for analysis of combinatorial compounds. Any other suitable analysis method is also optionally utilized. In this case, selection of reactants with different molecular weights for use in the first synthesis stage allows the unambiguous identification of test compounds. Compounds which are created using reactants with identical molecular weights in the first stage of synthesis may be differentiated based on differences in retention times in chromatography experiments, UV absorption, or the like.

These and other analytical techniques are described in, e.g., Chu et al. (1993) "Using affinity capillary electrophoresis to identify the peptide in a peptide library that binds most tightly to vancomycin," *J. Org. Chem.* 58:648–652, Fitch et al. (1994) "High-resolution (1)H NMR in solid-phase organic synthesis," *J. Org. Chem.* 59:7955–7956, Gao et al. (1996) "Screening derivatized peptide libraries for tight binding inhibitors to carbonic anhydrase II by electrospray ionization mass spectrometry," *J. Med. Chem.* 39:1949–1955, Keifer (1996) "Influence of resin structure, tether length, and solvent upon the high-resolution (1)H NMR spectra of solid-phase-synthesis resins," *J. Org. Chem.* 61:1558–1559, Metzger et al. (1993) "Ion-spray mass spectrometry and high-performance liquid chromatography. Mass spectrometry of synthetic peptide libraries," *Angew. Chem. Int. Ed.* 32:894–896, Stevanovic and Jung (1993) "Multiple sequence analysis: Pool sequencing of synthetic and natural peptide libraries," *Anal. Biochem.* 212:212–220, and Youngquist et al. (1994) "Matrix-assisted laser desorption ionization for rapid determination of the sequences of biologically active peptides isolated from support-bound combinatorial peptide libraries," *Rapid Commun. Mass Spectrom.* 8:77–81. Structural identification is described further below.

Structural Identification

The identity of a compound in a combinatorial library produced according to the methods described herein is determined by the sequence of reactions and choices of reactants used in each step of synthesis. The identity of a reactant used for the last (e.g., the third) stage of synthesis for each container is known by tracking this container to the reaction vessel used in the last stage of synthesis. The identity of reactants used in the previous (e.g., the second) stage of synthesis are optionally determined by tagging containers or preferably, by using the methods described in the co-pending patent application entitled "Structure Determination Methods Using Mass Measurement" by Sepetov et al., filed Feb. 2, 2001. These methods are described below. The identity of reactants used in the initial stage of synthesis are optionally determined by measuring certain physical properties of individual compounds such as mass, retention time in chromatography experiments, ultraviolet (UV) absorption, or the like.

In preferred embodiments, the structural identity of selected library members is determined according to methods that are based on mass measurements. The methods includes (a) providing a logical matrix or data structure representing virtual masses of members of a complex library (e.g., a combinatorial chemical library) produced by chemical or physical transformations of an initial set of chemical or physical members in which at least one group of the virtual masses includes complex library members having a shared chemical history. Optionally, multiple groups of the virtual masses include complex library members having shared chemical histories. The methods also include (b) correlating molecular mass measurements (e.g., mass spectrometric measurements) of two or more chemical or physical library members having a shared chemical history with two or more virtual masses in the logical matrix to identify one or more groups of virtual masses that most likely describe chemical or physical transformations undergone by the two or more chemical or physical library members. In certain embodiments, the one or more groups of virtual masses describe the chemical or physical transformations undergone by the two or more chemical or physical library members in (b). Additionally, the correlations in (b) generally account for one or more mass defects of reaction. Finally, the method includes (c) identifying the predicted or actual structures of the two or more chemical or physical library members within the one or more identified groups based one the molecular mass measurements. In preferred embodiments, the method is completely or partially computer implemented.

In certain embodiments, (a) includes solving a simultaneous system of equations to provide one or more values in the logical matrix. For example, solving the simultaneous system of equations optionally includes solving for one or more masses of one or more members of the initial set of chemical or physical members. Optionally, solving the simultaneous system of equations includes solving for one or more of: at least one mass of at least one member of the set of chemical or physical library members, at least one mass of at least one of the initial set of chemical or physical members, or at least one member of a set of expected mass changes.

In one embodiments, (b) includes (i) determining the molecular mass measurements for each of x members of a set of chemical or physical library members, wherein x is at least two, and wherein each x member is derived from one member of the initial set of chemical or physical members and comprises a shared chemical history with all other x members. This embodiment also includes (ii) subtracting a cumulative total mass of all members of the initial set of chemical or physical members from a cumulative total mass of all x members of the set of chemical or physical library members to determine a cumulative total mass change for the set of chemical or physical library members and (iii) dividing the cumulative total mass change by x to thereby determine a mass change for each of the x members of the set of chemical or physical library members. In addition, this embodiment includes (iv) subtracting the mass change of (iii) from each of the molecular mass measurements of (i) to thereby identify each member in the initial set of chemical or physical members corresponding to each individual x member of the set of chemical or physical library members.

In some embodiments, (a) includes calculating individual masses for each member of the logical matrix by separately summing masses for each member of the initial set of chemical or physical members with each mass in a set of expected mass changes, or by separately subtracting masses for each member of the initial set of chemical or physical members from each mass in the set of chemical or physical library members. Each calculated individual mass is assigned to one of m groups, m corresponding to a total number of individual mass changes in the set of expected mass changes. Furthermore, each of the m groups includes n members, n corresponding to a total number of members in the initial set of chemical or physical members.

Optionally, (b) includes (i) matching a selected mass from the set of chemical or physical library members with all identical calculated masses and excluding any of the m groups lacking a member n comprising a mass identical to the selected mass from further consideration to reduce a number of m groups available for subsequent consideration. Thereafter, the method typically includes (ii) repeating (i) at least once, in which each repeated (i) includes matching a different selected mass from the set of chemical or physical library members with all the identical calculated masses that remain in the reduced number of m groups from an immediately preceding (i) and excluding any of the reduced number of m groups lacking an n member with a mass identical to the different selected mass from further consideration to further reduce the number of m groups available for subsequent consideration. This method leads to (1) identifying a single m group which indicates that matched masses from the set of chemical or physical library members have a shared chemical history, (2) identifying more than one m group for further consideration which indicates that insufficient data exists for an unambiguous determination of whether masses selected from the set of chemical or physical library members have a shared chemical history, or (3) identifying no m group for further consideration which indicates that masses selected from the set of chemical or physical library members originate from materials lacking a shared chemical history.

In certain embodiments, the method further includes assigning each of the m groups a P variable in which each P variable is initially zero. In these embodiments, (b) includes (i) matching a selected mass from the set of chemical or physical library members with identical masses in each of the m groups in which the P variable for an m group is increased by one when the selected mass matches at least one value therein. Thereafter, these embodiments include (ii) repeating (i) for each remaining value in the set of chemical or physical library members, and (iii) determining which one or more m groups have highest P variables to identify one or more mass changes from the set of expected mass changes best fitting the set of chemical or physical library members. It also identifies all paired values in the initial set of chemical or physical members and the set of chemical or physical library members originating from materials with a shared chemical history.

These methods are typically implemented using a system for identifying predicted or actual structures for two or more members of a chemical or physical library. The system includes (a) at least one computer that includes a database having a logical matrix representing virtual masses of members of a complex library produced by chemical or physical transformations of an initial set of chemical or physical members in which at least one group of the virtual masses comprises complex library members having a shared chemical history. The system also includes (b) system software that includes one or more logic instructions for (i) correlating molecular mass measurements of two or more chemical or physical library members having a shared chemical history with two or more virtual masses in the logical matrix to identify one or more groups of virtual masses that most likely describe chemical or physical transformations undergone by the two or more chemical or physical library members. The correlations in (i) generally account for one or more mass defects of reaction. The system software also includes one or more logic instructions for (ii) identifying the predicted or actual structures of the two or more chemical or physical library members within the one or more identified groups based one the molecular mass measurements. In some embodiments, the one or more groups of virtual masses describe the chemical or physical transformations undergone by the two or more chemical or physical library members in (b). The system typically further includes a mass spectrometer or similar device operably connected to the at least one computer which provides the molecular mass measurements to be correlated. In addition, the system generally includes a handling system (e.g., a solid phase handler, such as a bead handler, a bead container handler, or the like) operably connected to the at least one computer, which handling system directs translocation and synthesis of the chemical or physical library members. The handling system generally includes at least one robotic armature. Combinatorial synthetic systems are described in greater detail below.

Solid Phase Synthesis Units

The solid phase synthesis units utilized in the methods of the invention include many alternative embodiments. For example, the solid phase synthesis units optionally each include a single particle independently selected from, e.g., a bead, a crown, a piece of paper, a piece of cotton, a piece of polymer, or the like. Optionally, the solid phase synthesis units each include multiple particles combined together. For example, an array or a container optionally includes multiple particles combined together. In certain embodiments, at least one of the multiple particles includes a non-functionalized solid support, whereas in others, at least one of the multiple particles includes a solid support having one or more functionalities attached thereto. In some embodiments, at least two of the multiple particles include solid supports having one or more identical or different functionalities attached thereto.

Suitable solid support materials include, but are not limited to, glass, polacryloylmorpholide, silica, controlled pore glass (CPG), polystyrene, polystyrene/latex, polyacyrlate, polyacrylamide, agar, agarose, chemically modified agars and agaroses, carboxyl modified teflon, nylon and nitrocellulose. The solid substrates can be biological, nonbiological, organic, inorganic, or a combination of any of these, existing as particles, strands, precipitates, gels, sheets, tubing, spheres, containers, capillaries, pads, slices, films, plates, slides, etc., depending upon the particular application. Other suitable solid substrate materials will be readily apparent to those of skill in the art.

Often, the surface of the solid substrate will contain reactive groups, such as carboxyl, amino, hydroxyl, thiol, or the like for the attachment of nucleic acids, proteins, etc. Surfaces on the solid substrate will sometimes, though not always, are composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. The surface may also be chemically modified or functionalized in such a way as to allow it to establish binding interactions with functional groups intrinsic to or specifically associated with the chemical materials to be immobilized.

For example, polymer beads (e.g., polystyrene, polypropylene, latex, nylon and many others), silica or silicon beads, clay or clay beads, ceramic beads, glass beads, magnetic beads, metallic beads, inorganic compound beads, and organic compound beads can be used. An enormous variety of solid support materials is commercially available, e.g., those typically used for chromatography (see, e.g., the 1999 Sigma "Biochemicals and Reagents for Life Sciences Research" Catalog from Sigma (Saint Louis, Mo.), e.g., pp. 1921–2007; The 1999 Suppleco "Chromatography Products" Catalogue, and others), as well as those commonly used for affinity purification (e.g., Dynabeads™ from Dynal, as well as many derivitized beads, e.g., various derivitized Dynabeads™ (e.g., the various magnetic Dynabeads™, which commonly include coupled reagents) supplied e.g., by Promega, the Baxter Immunotherapy Group, and many other sources).

Commercially available low pressure liquid chromatography media suitable as solid substrate material (i.e., material for making bead sets) in a variety of applications include, e.g., non-ionic macroreticular and macroporous resins which adsorb and release components based upon hydrophilic or hydrophobic interactions, such as Amberchrom resins (highly cross-linked styrene/divinylbenzene copolymers suitable for separation of peptides, proteins, nucleic acids, antibiotics, phytopharmacologicals, and vitamins); the related Amberlite XAD series resins (polyaromatics and acrylic esters) and amberchroms (polyaromatic and polymethacrylates) (manufactured by Rohm and Haas, available through Suppleco); Diaion (polyaromatic or polymethacrylic beads); Dowex (polyaromatics or substituted hydrophilic functionalized polyaromatics) (manufactured by Dow Chemical, available through Suppleco); Duolite (phenol-formaldehyde with methanolic functionality), MCI GEL sephabeads, supelite DAX-8 (acrylic ester) and Supplepak (polyaromatic) (all of the preceding materials are available from Suppleco). For a description of uses for Amberlite and Duolite resins, see, Amberlite/Duolite Anion Exchange Resins (Available from Suppleco, 1997 Cat No. T412141). Gel filtration chromatography matrixes are also suitable as solid phase materials, including e.g., for bead formation, including sephacryl, sephadex, sepharose, superdex, superose, toyopearl, agarose, cellulose, dextrans, mixed bead resins, polystyrene, nuclear resins, DEAE cellulose, Benzyl DEA cellulose, TEAE cellulose, and the like (Suppleco).

A variety of affinity media for purification and separation of molecular components are also available, including a variety of modified silica gels available from SIGMA, Aldrich and SIGMA-Aldrich, as well as Suppleco, such as acrylic beads, agarose beads, Mono beads, cellulose, sepharose, sepharose CL, toyopearl or the like chemically linked to an affinity ligand such as a biological molecule. A wide variety of activated matrixes, amino acid resins, avidin and biotin resins, carbohydrate resins, dye resins, glutathione resins, hydrophobic resins, immunochemical resins, lectin resins, nucleotide/coenzyme resins, nucleic acid resins, and specialty resins are available, e.g., from Suppleco, SIGMA, Aldrich or the like. See also, Hermanson et al. (1992) Immobilized Affinity Ligand Techniques Academic Press.

As mentioned, suitable solid supports for the methods described herein are well-known in the art. Solid supports and support derivation are described further in, e.g., Santini et al. (1998) "A Measure of Solvent Effects on Swelling of Resins for Solid Phase Organic Synthesis," *Tetrahedron Lett.* 39:8951–8954, Labadie (1998) "Polymeric Supports for Solid Phase Synthesis," *Curr. Opin. Chem. Biol.* 2:346–352, Zhao et al. (1999) "Polystyrene Grafted Fluoropolymer MicroTubes: New Supports for Solid-Phase Organic Synthesis with Useful Performance at High Temperature," *Combinatorial Chemistry* 1:91–95, Stranix et al. (1997) "Functional polymers from (vinyl)polystyrene: Recyclable polymer-supported organosilicon protecting groups for solid-phase synthesis," *J. Org. Chem.* 62:6183–6186, Gooding et al. (1999) "On the Development of New Poly(styrene-oxyethylene) Graft Copolymer Resin Supports for Solid-Phase Organic Synthesis," *J. Combinatorial Chemistry* 1:113–122, Toy and Janda (1999) "New supports for solid-phase organic synthesis: development of polystyrene resins containing tetrahydrofuran derived crosslinkers," *Tetrahedron Lett.* 40(35):6329–6332, Mahajan et al. (1999) "Resin-bound dendrimers as high loading supports for solid phase chemistry," *Tetrahedron Lett.* 40(26):4909–4912, and Hird et al. "Polymer discs—an alternative support format for solid phase synthesis," (1999) *Tetrahedron Lett.* 55(31):9575–9584.

Linkers and Linking Chemistries

The chemical components of the invention are optionally presented on solid or semi-solid supports via any of a variety of linking chemistries (they are, alternately, directly attached to the supports, e.g., by any available chemical or physical method), allowing the incorporation of biological and chemical components of interest into the solid supports. As described further above, a wide variety of organic and inorganic polymers, both natural and synthetic may be employed as the material for the solid surface. Illustrative polymers include polyethylene, polypropylene, poly(4-methylbutene), polystyrene, polymethacrylate, poly (ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include papers, ceramics, such as glass, metals, metalloids, semiconductive materials, cements, or the like. In addition, substances that form gels, such as proteins (e.g., gelatins), lipopolysaccharides, silicates, agarose and are also optionally used.

A wide variety of linking chemistries are available for linking molecules to a wide variety of solid or semi-solid support elements. It is impractical and unnecessary to describe all of the possible known linking chemistries for linking molecules to a solid support. It is expected that one of skill can easily select appropriate chemistries, depending on the intended application. However, for purposes of illustration certain linkers and linkage chemistries are described. For example, in certain embodiments, solid supports of the invention optionally include silicate elements (e.g., glass or silicate beads). Silicon-based molecules appropriate for functionalizing surfaces are commercially available. See, e.g., Silicon Compounds Registry and Review, United Chemical Technologies, Bristol, Pa. Additionally, the art in this area is very well developed and those of skill will be able to choose an appropriate molecule for a given purpose. Appropriate molecules can be purchased commercially, synthesized de novo, or it can be formed by modifying an available molecule to produce one having the desired structure and/or characteristics.

The substrate linker attaches to the solid substrate through any of a variety of chemical bonds. For example, the linker is optionally attached to the solid substrate using carbon-carbon bonds, for example via substrates having (poly) trifluorochloroethylene surfaces, or siloxane bonds (using, for example, glass or silicon oxide as the solid substrate). Siloxane bonds with the surface of the substrate are formed in one embodiment via reactions of derivatization reagents bearing trichlorosilyl or trialkoxysilyl groups. The particular linking group is selected based upon, e.g., its hydrophilic/ hydrophobic properties where presentation of an attached polymer in solution is desirable. Groups which are suitable for attachment to a linking group include amine, hydroxyl, thiol, carboxylic acid, ester, amide, isocyanate and isothiocyanate. Preferred derivatizing groups include aminoalkyltrialkoxysilanes, hydroxyalkyltrialkoxysilanes, polyethyleneglycols, polyethyleneimine, polyacrylamide, polyvinylalcohol and combinations thereof.

The components which can be attached to a derivitized surface include peptides, nucleic acids, mimetics, large and small organic molecules, polymers, or the like. For example, moieties bearing a permanent charge or a pH dependent charge are useful in practicing the present invention. For example, the charged group can be a carboxylate, quaternary amine or protonated amine that is a component of an amino acid that has a charged or potentially charged side chain. The amino acids can be either those having a structure which occurs naturally or they can be of unnatural structure (i.e., synthetic). Useful naturally occurring amino acids include, arginine, lysine, aspartic acid and glutamic acid. Surfaces utilizing a combination of these amino acids are also of use in the present invention. Further, peptides comprising one or more residues having a charged or potentially charged side chain are useful coating components and they can be synthesized utilizing arginine, lysine, aspartic acid, glutamic acid and combinations thereof. Useful unnatural amino acids are commercially available or can be synthesized utilizing art-recognized methodologies. In those embodiments in which an amino acid moiety having an acidic or basic side chain is used, these moieties can be attached to a surface bearing a reactive group through standard peptide synthesis methodologies or easily accessible variations thereof. See, e.g., Jones, *Amino Acid and Peptide Synthesis*, Oxford University Press, Oxford, 1992.

Linking groups can also be placed on the solid supports of the invention. Linking groups of use in the present invention can have a range of structures, substituents and substitution patterns. They can, for example be derivitized with nitrogen, oxygen and/or sulfur containing groups which are pendent from, or integral to, the linker group backbone. Examples include, polyethers, polyacids (polyacrylic acid, polylactic acid), polyols (e.g., glycerol, ), polyamines (e.g., spermine, spermidine) and molecules having more than one nitrogen, oxygen and/or sulfur moiety (e.g., 1,3-diamino-2-propanol, taurine). See, e.g., Sandler et al. *Organic Functional Group Preparations,* 2nd Ed., Academic Press, Inc. San Diego 1983. A wide range of mono-, di- and bis-functionalized poly(ethyleneglycol) molecules are commercially available and will prove generally useful in this aspect of the invention. See, e.g., 1997–1998 Catalog, Shearwater Polymers, Inc., Huntsville, Ala. Additionally, those of skill in the art have available a great number of easily practiced, useful modification strategies within their synthetic arsenal. See, e.g., Harris, *Rev. Macromol. Chem. Phys.*, C25(3):325–373 (1985); Zalipsky et al., *Eur. Polym. J.,* 19(12):1177–1183 (1983); U.S. Pat. No. 5,122,614, issued Jun. 16, 1992 to Zalipsky; U.S. Pat. No. 5,650,234, issued to Dolence et al. Jul. 22, 1997, and references therein.

In certain embodiments of the invention, the coupling chemistries for coupling materials to the solid supports of the invention are light-controllable, i.e., utilize photo-reactive chemistries. The use of photo-reactive chemistries and masking strategies to activate coupling of molecules to substrates, as well as other photo-reactive chemistries is generally known (e.g., for semi-conductor chip fabrication and for coupling bio-polymers to solid phase materials). The use of photo-cleavable protecting groups and photo-masking permits type switching of both mobile and fixed array members, i.e., by altering the presence of substrates present on the array members (i.e., in response to light). Among a wide variety of protecting groups which are useful are nitroveratryl (NVOC) -methylnitroveratryl (Menvoc), allyloxycarbonyl (ALLOC), fluorenylmethoxycarbonyl (FMOC), -methylnitro-piperonyloxycarbonyl (MeNPOC), -NH-FMOC groups, t-butyl esters, t-butyl ethers, and the like. Various exemplary protecting groups (including both photo-cleavable and non-photo-cleavable groups) are described in, e.g., Atherton et al., (1989) *Solid Phase Peptide Synthesis*, IRL Press, and Greene, et al. (1991) *Protective Groups In Organic Chemistry*, 2nd Ed., John Wiley & Sons, New York, N.Y., as well as, e.g., Fodor et al. (1991) *Science*, 251:767–777, Wang (1976) *J. Org. Chem.* 41:3258; and Rich, et al. (1975) *J. Am. Chem. Soc.* 97:1575–1579. The use of these and other photo-cleavable linking groups for nucleic acid and peptide synthesis on solid supports is a well-established methodology.

Additional details relating to linkers and linkage chemistries is provided in, e.g., Alonso et al. (2000) "b-Dimethylphenylsilylethyl esters: A linker for solid-phase chemistry," *Tetrahedron Lett.* 41:5617–5622, Berst et al. (2000) "A latent aryl hydrazine 'safety-catch' linker compatible with N-alkylation," *Tetrahedron Lett.* 41:6649–6653, Blanco et al. (2000) "Solid phase Diels-Alder/retro Diels-Alder reactions. A new method for traceless linker strategy," *Tetrahedron Lett.* 41:7875–7878, and Blaney et al. (2000) "Solid-phase synthesis of tertiary methylamines via reductive alkylation-fragmenation using a hydroxylamine linker," *Tetrahedron Lett.* 41:6635–6638.

Components and Library of Materials

Essentially any organic or inorganic compound is optionally formed according to the methods described herein. As a consequence, no attempt is made herein to describe all of the possible reagents or components, or combinatorial compounds optionally utilized and/or synthesized. However, for purposes of illustration, but not for limitation, certain general classes of reagents and/or combinatorial compounds are mentioned as follows.

Organic compounds include of carbon and hydrogen, with or without oxygen, nitrogen or other elements, except those in which carbon does not play a critical role (e.g., carbonate salts). Examples of organic compounds that are optionally synthesized using the methods described herein include, but are not limited to, biological (nucleic acids, peptides, polypeptides, lipids, carbohydrates, or the like) or non-biological polymers. Polymers include, e.g., nonmetallic materials that include large macromolecules composed of many repeating units. These materials are optionally natural or synthetic and cross-linked or non-crosslinked. They are optionally homopolymers, copolymers, or higher-ordered polymers. Examples of polymers that are optionally prepared using the methods of the present invention include, but are not limited to, the following: polyurethanes, polyesters, polycarbonates, polyethyleneimines, polyacetates, polystyrenes, polyamides, polyanilines, polyacetylenes, polypyrroles, or the like. Organometallic compounds are also optionally prepared using the methods of the present invention. These include a class of compounds of the type R-M in which carbon atoms are linked directly with metal atoms.

In contrast, inorganic compounds do not contain carbon as a principal element. The oxides and sulphides of carbon and the metallic carbides are considered inorganic materials. Additional examples of inorganic compounds that are optionally synthesized using the methods described herein include, but are not limited to, intermetallics, metal alloys, ceramics, and magnetic alloys.

Various composite materials are also optionally prepared according to the methods described herein. Composite materials include, e.g., any combination of two materials differing in form or composition on a macroscale. They are optionally inorganic, organic or a combination thereof. They also include, e.g., doped materials, dispersed metal catalysts and other heterogeneous solids.

The reagents and/or combinatorial compounds of the invention are typically covalent network solids, ionic solids, or molecular solids. A covalent network solid typically includes atoms held together in a large network of chains by covalent bonds. An ionic solid is generally modeled as cations and anions held together by electrical attraction of opposite charge. Finally, a molecular solid typically includes atoms or molecules held together by intermolecular forces.

Combinatorial Synthesis Systems

The present invention also provides a combinatorial library synthesis system for synthesizing combinatorial libraries according the methods described herein. The system generally includes a plurality of reaction vessels (e.g., flasks, test tubes, wells of one or more microwell plates, or the like), a handling system (including, e.g., a bead handler, etc.) configured to translocate solid phase synthesis units (e.g., individual beads, tea-bags, or other containers having multiple beads or other solid supports disposed therein) and/or reagents to and from the plurality of reaction vessels, a detection system (e.g., a mass spectrometer or the like) to detect one or more distinguishing physical properties (e.g., different masses or the like) of selected members of the combinatorial library, and a computer (e.g., an information appliance, digital device, or the like) operably connected to the handling and detection systems.

For example, the system optionally includes system software (e.g., on a computer which is operably coupled to or part of the system) which directs the handling or detection systems to: (i) segregate the solid phase synthesis units into n separate first stage reaction vessels to provide m*f solid phase synthesis units in each of the n vessels in which n is equal to a number of choices of different first components in a first stage of a library synthesis, m is equal to a number of choices of different second components in a second stage of the library synthesis, and f is equal to a number of solid phase synthesis units which comprise identical materials on completion of the library synthesis.

The system software also optionally directs the handling or detection systems to: (ii) deliver one or more of the different first components to each of the n separate first stage reaction vessels to provide for reaction of the different first components with the solid phase synthesis units to provide first stage reacted solid phase members and (iii) segregate the first stage reacted solid phase members from the n separate first stage reaction vessels into m separate second stage reaction vessels by distributing at least one of the first stage reacted solid phase members from each of the separate first stage reaction vessels into each second stage reaction vessels such that each second stage reaction vessel comprises at least n*f solid phase synthesis units.

In addition, the system software also optionally directs the handling or detection systems to: (iv) deliver one or more different second components to the second stage reaction vessels to provide for reaction of the different second components with the first stage reacted solid phase members to provide the combinatorial library and (v) detect one or more distinguishing physical properties (e.g., different masses or the like) of the selected members of the combinatorial library. The system software also optionally directs the handling system in (iv) to effect cleavage of combinatorial library members from the solid phase synthesis units (e.g., by delivering any appropriate cleavage reagent or other cleavage inducing component, such as light, heat or other forms of energy).

In certain embodiments prior to (i), the system software directs the handling system to: (1) segregate at least n*m*f solid phase synthesis units into p separate third stage reaction vessels in which is equal to a number of choices of different third components in a third stage of the library synthesis, and in which each separate third stage reaction vessel comprises the at least n*m*f/p solid phase synthesis units and (2) deliver one or more of the different third components to each of the separate third stage reaction vessels to provide for reaction of the different third components with the solid phase synthesis units to provide third stage reacted solid phase members, and (3) combine and mix the third stage reacted solid phase members in a single pool to provide the solid phase synthesis units for (i). Optionally, the at least n*m*f solid phase synthesis units include n*m*f*p solid phase synthesis units. In some embodiments, the system software further directs the handling system to: (4) separate the solid phase synthesis units of (3) into n*m separate containers in which the n*m separate containers are segregated into the n separate first stage reaction vessels as the solid phase synthesis units of (i). Optionally, the system software further directs the handling system to separate the solid phase synthesis units of (3) into n*m separate containers in which the n*m separate containers are segregated into the m separate second stage reaction vessels as the solid phase synthesis units of (iii). As an additional option, each of the n*m separate containers comprises multiple support materials combined together.

FIG. 4A schematically illustrates certain steps described above which are directed by the system software. As shown, in A1 the system software directs the handling system to segregate solid phase synthesis units into n separate first stage reaction vessels to provide m*f solid phase synthesis units in each of the n vessels and in A2 to deliver different first components to each of the n separate first stage reaction vessels to yield first stage reacted solid phase members following reaction of the different first components with the solid phase synthesis units. As further shown in A3, the software also directs the handling system to segregate the first stage reacted solid phase members from the n separate first stage reaction vessels into m separate second stage reaction vessels by distributing at least one of the first stage reacted solid phase members from each of the separate first stage reaction vessels into each second stage reaction vessel and in A4 to deliver different second components to the second stage reaction vessels to yield the combinatorial library following reaction of the different second components with the first stage reacted solid phase members. In A5, the system software directs the detection system to detect distinguishing physical properties of selected members of the combinatorial library (e.g., via mass spectroscopy or otherwise).

FIG. 4B schematically illustrates certain additional steps performed by the handling system under the control of system software in one embodiment of the invention described above. Steps B1 through B3 are optionally performed by the system prior to performing step A1, depicted in FIG. 4A. As shown, in B1 the system software directs the handling system to segregate the at least n*m*f solid phase synthesis units into p separate third stage reaction vessels such that each separate third stage reaction vessel includes at least n*m*f/p solid phase synthesis units. In step B2, the software directs handling system to the deliver different third components to each of the separate third stage reaction vessels to yield third stage reacted solid phase members following reaction of the different third components with the solid phase synthesis units. Finally, in step B3, the software directs the handling system to combine and mix the third stage reacted solid phase members in a single pool to provide the solid phase synthesis units for A1.

In preferred embodiments, the computer further includes at least one database having a logical matrix corresponding to masses of members of a virtual library that are correlated with the detected masses of the combinatorial library members produced by the system to thereby identify chemical structures of the combinatorial library members. Correlations typically account for mass defects of reaction of the detected masses, e.g., to increase the accuracy of structural identifications. At least one entry in the logical matrix typically includes a summation of masses of different combinations of first and second components. In certain embodiments, all entries include mass summations, whereas in others, matrix entries include equations for solving for assorted parameters, including masses of, e.g., at least one mass of at least one member of the set of chemical or physical library members, at least one mass of at least one of the initial set of chemical or physical members, or at least one member of a set of expected mass changes. Further details regarding this approach are found in co-filed application "Structure Identification Methods Using Mass Measurements" by Sepetov et al., U.S. Ser. No. 6,625,546.

Additional details relating to the automation of combinatorial synthetic methods are described in, e.g., Cargill and Maiefski (1996) "Automated combinatorial chemistry on solid phase," *Lab. Robotics. Automation* 8:139–148, Zuckermann et al. (1992) "Design, construction and application of a fully automated equimolar peptide mixture synthesizer," *Int. J. Peptide Prot. Res.* 40:497–506, Castelino et al. (2000) "Automated sample storage for drug discovery," *Chim. Oggi.* 17:32–35, Davis and Swayze (2000) "Automated solid-phase synthesis of linear nitrogen-linked compounds," *Biotechnol. Bioeng.* 71:19–27, Groger et al. (2000) "1,3,5-Triazines, versatile industrial building blocks: Synthetic approaches and applications," *Chim. Oggi.* 18:12–16, Haag (2000) "Chemspeed Ltd.: Automated and unattended parallel synthesis integrating work-up and analysis," *Chimia* 54:163–164, Hu et al. (2000) "Automated solid-phase synthesis and photophysical properties of oligodeoxynucleotides labeled at 5'-aminothymidine with Ru(bpy)(2)(4-m-4'-cam-bpy)(2+)," *Inorg. Chem.* 39:2500–2504, Lewis et al. (2000) "Automated high-throughput quantification of combinatorial arrays," *American Pharmaceutical Review* 3:63–68, North (2000) "Implementation of analytical technologies in a pharmaceutical development organization-looking into the next millennium," *Journal of Automated Methods and Management in Chemistry* 22:41–45, and Keifer et al. (2000) "Direct-injection NMR (DI-NMR): A flow NMR technique for the analysis of combinatorial chemistry libraries," *Journal of Combinatorial Chemistry* 2; 151–171.

Controllers

The handling systems of the invention typically incorporate one or more controllers, either as separate or integral components, which are generally utilized, e.g., to regulate the quantities of reagents dispensed, and the segregation and distribution of solid phase synthesis units. A variety of available robotic elements (robotic arms, movable platforms, etc.) can be used or modified for these purposes.

For example, controllers typically direct dipping of bead handling elements of the handling systems into, e.g., selected wells on microwell plates, or other reaction vessels, to dispense or extract, e.g., selected beads or other solid phase synthesis units. Typically, the controller systems of the present invention are appropriately configured to receive or interface with a reaction vessel or system element as described herein. For example, the controller and/or detector, optionally includes a stage upon which the reaction vessels of the invention are disposed or mounted to facilitate appropriate interfacing among, e.g., a bead handler and/or detector and a particular reaction vessel. Typically, the stage includes an appropriate mounting/alignment structural element, such as alignment pins and/or holes, a nesting well, or the like to, e.g., facilitate proper device alignment.

Figure 5A:
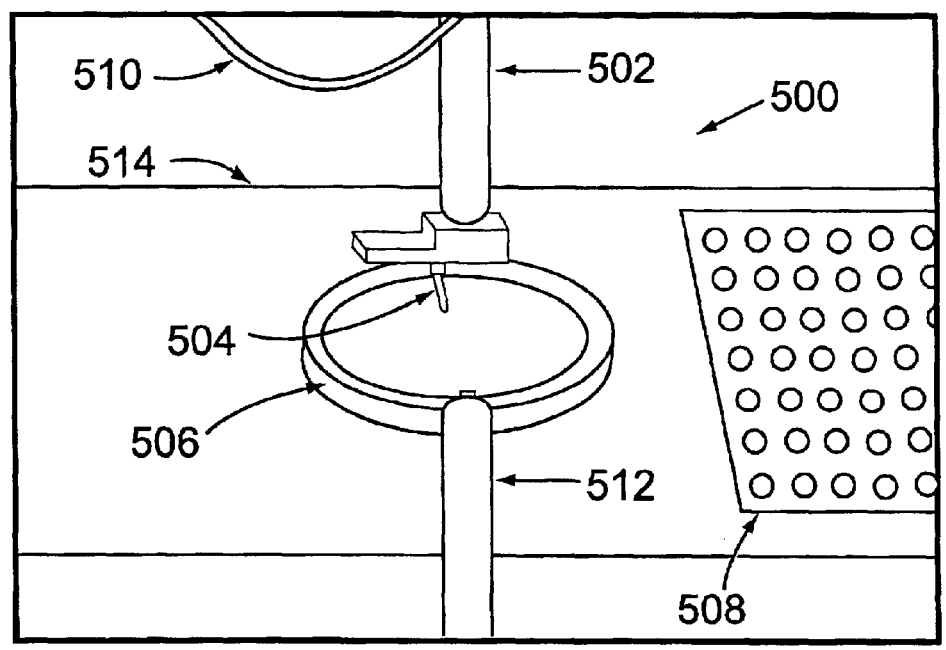
FIG. 5A schematically depicts certain aspects of a handling system.
Figure 5B:
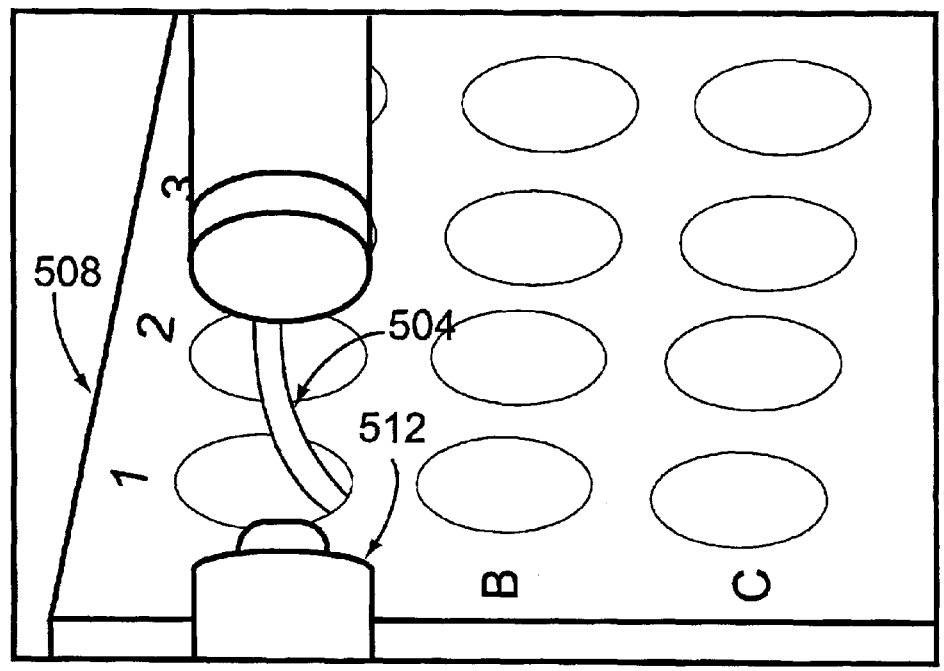
FIG. 5B schematically shows a bead handler of one embodiment of a handling system distributing single beads to a well of a microwell plate.

FIG. 5A schematically depicts aspects of one example of a bead handling system. As shown, handling system 500 includes robotic armature 502. The handling system is depicted with bead handler 504 hunting for beads in pooling vessel 506 for distribution to the wells of microwell plate 508. Robotic armature 502 is operably connected via connection 510 to at least one controller (not shown). Detector 512 is also included in this embodiment. As also shown, pooling vessel 506 and microwell plate 508 are disposed on stage 514. FIG. 5B schematically illustrates a magnified view of bead handler 504 distributing beads to a well of microwell plate 508. Detector 512 is also depicted.

Detector

In preferred embodiments, mass is the distinguishing physical property utilized, e.g., to identify the structure of a selected synthesis product as described herein. Mass is detected via mass spectrometric methods. Mass spectrometry is a widely used analytical technique that is typically used to provide information about, e.g., the isotopic ratios of atoms in samples, the structures of various molecules, including biologically important molecules (e.g., transporter molecules, transmitters, enzymes, receptors, chemotactic factors, and the like), and the qualitative and quantitative composition of complex mixtures. Common mass spectrometer systems include a system inlet, an ion source, a mass analyzer, and a detector which are under vacuum. The detector is typically operably connected to a signal processor and a computer. Desorption ion sources for use in the present invention, include field desorption (FD), electrospray ionization (ESI), chemical ionization, matrix-assisted desorption/ionization (MALDI), plasma desorption (PD), fast atom bombardment (FAB), secondary ion mass spectrometry (SIMS), and thermospray ionization (TS).

Mass spectrometry is well-known in the art. In particular, mass spectrometry techniques for solid-phase synthesis are described in, e.g., Enjalbal et al., (2000) "Mass spectrometry in combinatorial chemistry," *Mass Spectrom. Rev.* 19:139–161, Lake et al. (2000) "Sample preparation for high throughput accurate mass analysis by matrix-assisted laser desorption/ionization time-of-flight mass spectrometry," *Rapid Commun. Mass Spectrom.* 14:1008–1013, Brummel et al. (1996) "Evaluation of Mass Spectrometric Methods Applicable to the Direct Analysis of Non-Peptide Bead-Bound Combinatorial Libraries," *N. Anal. Chem.* 68:237–242, Hughes (1998) "Design of self-coded combinatorial libraries to facilitate direct analysis of ligands by mass spectrometry," *Med. Chem.* 41:3804–3811, Carrasco et al. (1997) "Direct Monitoring of Organic Reactions on Polymeric Supports," *Tetrahedron Lett.* 38:6331–6334, Berlin et al. (1997) "Spectrometrically Monitored Selection Experiments-Quantitative Laser Desorption Mass Spectrometry of Small Chemical Libraries," *Chem. Biol.* 4:63–77, Newcomb et al. (1998) "Analysis of 9-fluorenylmethoxycarbonyl (Fmoc) loading of solid-phase synthesis resins by gas chromatography," *Biotech. Bioeng.* (Comb. Chem.) 61:55–60, Demirev and Zubarev (1997) "Probing combinatorial library diversity by mass spectrometry," *Anal. Chem.* 69:2893–2900, Haap et al. (1998) "FT-IR Mapping—A New Tool for Spatially-Resolved Characterization of Polymer-Bound Combinatorial Compound Libraries with Ir Microscopy," *Angew. Chem. Int. Ed.* 37(23):3311–3314, Schriemer et al. (1998) "Microscale Frontal Affinity-Chromatography with Mass-Spectrometric Detection—A New Method for the Screening of Compound Libraries," *Angew. Chem. Int. Ed.* 37(24): 3383–3387, and van Breemen et al. (1997) "Pulsed ultrafiltration mass spectrometry: A new method for screening combinatorial libraries," *Anal. Chem.* 69:2159–2164. General sources of information about mass spectrometry include, e.g., Skoog, et al. *Principles of Instrumental Analysis* ($5^{th}$ Ed.) Hardcourt Brace & Company, Orlando (1998).

The systems of the present invention optionally include various other signal detectors, e.g., which detect concentration, fluorescence, phosphorescence, radioactivity, pH, charge, absorbance, refractive index, luminescence, temperature, magnetism, or the like. The detector(s) optionally monitors one or a plurality of signals from upstream and/or downstream of the performance of a given synthesis step. For example, the detector optionally monitors a plurality of optical signals, which correspond in position to "real time" results. Example detectors or sensors include photomultiplier tubes, CCD arrays, optical sensors, temperature sensors, pressure sensors, pH sensors, conductivity sensors, scanning detectors, or the like. The detector optionally moves relative to assay components, or alternatively, assay components, such as samples of selected synthesis products move relative to the detector. Optionally, the systems of the present invention include multiple detectors. Each of these types of sensors is optionally readily incorporated into the systems described herein. In these systems, such detectors are typically placed either in or adjacent to, e.g., a particular reaction vessel, such that the detector is within sensory communication with the reaction vessel. The phrase "within sensory communication" of a particular region or element, as used herein, generally refers to the placement of the detector in a position such that the detector is capable of detecting the property of the reaction vessel or portion thereof, the contents of a portion of the vessel, or the like, for which that detector was intended. The detector optionally includes or is operably linked to a computer, e.g., which has system software for converting detector signal information into assay result information or the like.

The detector optionally exists as a separate unit, or is integrated with the handling or controller system, into a single instrument. Integration of these functions into a single unit facilitates connection of these instruments with the computer (described below), by permitting the use of few or a single communication port(s) for transmitting information between system components.

Specific detection systems that are optionally used in the present invention (e.g., in addition to, or in lieu of, a mass spectrometer) include, e.g., an emission spectroscope, a fluorescence spectroscope, a phosphorescence spectroscope, a luminescence spectroscope, a spectrophotometer, a photometer, a nuclear magnetic resonance spectrometer, an electron paramagnetic resonance spectrometer, an electron spin resonance spectroscope, a turbidimeter, a nephelometer, a Raman spectroscope, a refractometer, an interferometer, an x-ray diffraction analyzer, an electron diffraction analyzer, a polarimeter, an optical rotary dispersion analyzer, a circular dichroism spectrometer, a potentiometer, a chronopotentiometer, a coulometer, an amperometer, a conductometer, a gravimeter, a thermal gravimeter, a titrimeter, a differential scanning colorimeter, a radioactive activation analyzer, a radioactive isotopic dilution analyzer, or the like.

Computers

As noted above, the systems of the present invention typically include a computer (or other information appliance) operably connected to or included within various system components. As described herein, the computer typically includes system software that directs the handling and detection systems to, e.g., segregate or distribute solid phase synthesis units into selected reaction vessels, deliver various reagents (e.g., different components or building blocks, scaffolds, or the like) to selected reaction vessels, detect distinguishing physical properties of selected members of combinatorial libraries, or the like. Additionally, the handling/controller system and/or the detection system is/are optionally coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention by inputting character strings corresponding to reagents or masses thereof. For example, the systems optionally include the foregoing software having the appropriate character string information, e.g., used in conjunction with a user interface (e.g., a GUI in a standard operating system such as a Windows, Macintosh or LINUX system) to manipulate strings of characters.

The computer can be, e.g., a PC (Intel x86 or Pentium chip-compatible DOS™, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for performing the methods described herein is optionally easily constructed by one of skill using a standard programming language such as Visual basic, Fortran, Basic, Java, or the like. Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation, e.g., varying or selecting the rate or mode of movement of various system components, directing X-Y-Z translation of the bead handler, or of one or more microwell plates or other reaction vessels, or the like. The computer then receives the data from the one or more sensors/detectors included within the system, and interprets the data, either provides it in a user understood format, or uses that data to initiate further controller instructions, in accordance with the programming, e.g., such as in monitoring reaction temperatures or the like.

In addition, one approach for refining a system's ability to recognize patterns in data sets, or refine such pattern recognition is to use a heuristic learning approach, a neural network approach and/or a genetic algorithm to refine such models. By using such predictive system components, the systems gradually becomes more efficient at selecting "correct" masses, or, e.g., predicting whether any discrepancy between actual and predicted masses is constant, or observing any trends or principle data components, or the like. A variety of approaches can be used to manipulate or consider data in a system, including principle component analysis, use of positive or negative data, data parameterization, consideration of whether predictions meet observed phenomena use of genetic algorithms, neural networks or other heuristic learning components, etc.

For example, Partek Incorporated (St. Peters, Mo.; www.partek.com) provides software for pattern recognition (e.g., which provide Partek Pro 2000 Pattern Recognition Software) which can be applied to genetic algorithms for multivariate data analysis, interactive visualization, variable selection, neural & statistical modeling. Relationships can be analyzed, e.g., by Principal Components Analysis (PCA) mapped scatterplots and biplots, Multi-Dimensional Scaling (MDS) mapped scatterplots, Star plots, etc. Further information regarding genetic algorithms and neural networks can be found in David E. Goldberg (1989) *Genetic Algorithms in Search, Optimization and Machine Learning* Addison-Wesley Pub Co; ISBN: 0201157675; Timothy Masters (1993) *Practical Neural Network Recipes in C++ (Book&Disk edition)* Academic Pr; ISBN: 0124790402; Kevin Gurney (1999) *An Introduction to Neural Networks*, UCL Press, 1 Gunpowder Square, London EC4A 3DE, UK; Christopher M. Bishop (1995) *Neural Networks for Pattern Recognition* Oxford UNIV Press; ISBN: 0198538642; Brian D. Ripley, N. L. Hjort (Contributor) (1995) *Pattern Recognition and Neural Networks* Cambridge Univ Pr (Short); ISBN: 0521460867 and in a variety of other currently available references. Additional details regarding computing systems of the present invention are described below.

Example Combinatorial Synthesis System

Figure 6:
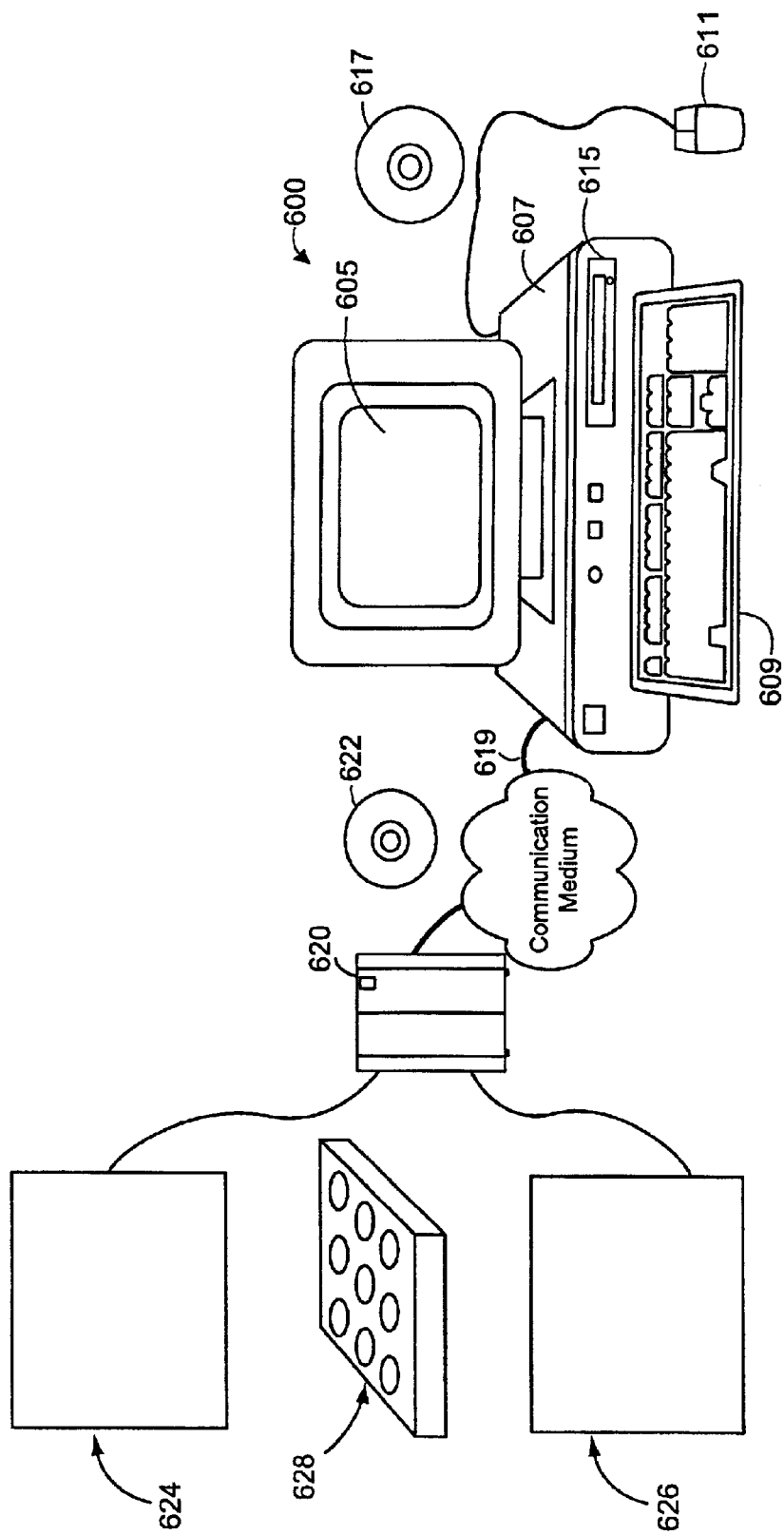
FIG. 6 schematically shows one embodiment of a combinatorial synthesis system.

FIG. 6 is a block diagram showing a representative example combinatorial synthesis system including a logic device in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform according to the invention. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

FIG. 6 shows information appliance or digital device 600 that may be understood as a logical apparatus that can read instructions from media 617 and/or network port 619, which can optionally be connected to server 620 having fixed media 622. Apparatus 600 can thereafter use those instructions to direct server or client logic, as understood in the art, to embody aspects of the invention. One type of logical apparatus that may embody the invention is a computer system as illustrated in 600, containing CPU 607, optional input devices 609 and 611, disk drives 615 and optional monitor 605. Fixed media 617, or fixed media 622 over port 619, may be used to program such a system and may represent a disk-type optical or magnetic media, magnetic tape, solid state dynamic or static memory, or the like. In specific embodiments, the invention may be embodied in whole or in part as software recorded on this fixed media. Communication port 619 may also be used to initially receive instructions that are used to program such a system and may represent any type of communication connection. Optionally, the invention is embodied in whole or in part within the circuitry of an application specific integrated circuit (ACIS) or a programmable logic device (PLD). In such a case, the invention may be embodied in a computer understandable descriptor language, which may be used to create an ASIC, or PLD.

FIG. 6 also includes handling system 624 and detection system 626, both of which are operably connected to digital device 600 via server 620. Optionally, handling system 624 and/or detection system 626 are directly connected to digital device 600. During operation, handling system 624 typically distributes reagents and/or solid phase synthesis units (e.g., individual beads, tea-bags, or other reaction containers) to various reaction vessels, such as microwell plate 628 which includes a plurality of reaction vessels (i.e., wells) disposed therein. Between synthetic steps, handling system 624 generally pools and/or segregates solid phase synthesis units for additional rounds of synthesis or for product analysis.

Detection system 626 generally includes a mass spectrometer for detecting masses of selected members of a combinatorial library following synthesis. Digital device 600 digitizes, stores, and manipulates signal information detected by detection system 626 using one or more logic instructions. In preferred embodiments, system software operating in digital device 600 correlates detected masses of synthesized library members with a logical matrix of virtual masses stored on, e.g., fixed media 617 or on fixed media 622 to identify structures corresponding to selected synthesized library members.

Kits

The present invention also provides kits that typically include systems, system software, modules, and workstations for performing the combinatorial synthetic and structural identification methods described herein. In certain embodiments, a kit includes only system software. A kit optionally contains additional components for the assembly and/or operation of a multimodule workstation of the invention including, but not restricted to robotic elements (e.g., a track robot, a robotic armature, or the like), reagent, solid phase synthesis unit, and/or reaction vessel handling devices, and computers (including, e.g., input/output devices, CPUs, or the like). Kits are optionally packaged to include reagents, control/calibrating materials, solid phase synthesis units, and/or reaction vessels for performing the methods of the invention. In the case of pre-packaged reagents, the kits optionally include pre-measured or pre-dosed reagents that are ready to incorporate into the synthetic methods without measurement, e.g., pre-measured fluid aliquots, or pre-weighed or pre-measured solid reagents that can be easily reconstituted by the end-user of the kit. Generally, reagents are provided in a stabilized form, so as to prevent degradation or other loss during prolonged storage, e.g., from leakage. A number of stabilizing processes are widely used for reagents that are to be stored, such as the inclusion of chemical stabilizers (i.e., enzymatic inhibitors, microcides/bacteriostats, anticoagulants), the physical stabilization of the material, e.g., through immobilization on a solid support, entrapment in a matrix (i.e., a gel), lyophilization, or the like. Kits typically include appropriate instructions for using the reagents, practicing the methods, and operating the systems. Kits also typically include packaging materials or containers for holding kit components.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of identifying selected members of a synthesized library of materials, comprising:
    (a) providing at least n*m*f solid phase synthesis units, wherein n is equal to a number of choices of different first components in a first stage of synthesis, m is equal to a number of choices of different second components in a second stage of the synthesis, and f is equal to a number of solid phase synthesis units to comprise identical materials upon completion of the synthesis;
    (b) segregating the solid phase synthesis units into n separate first stage reaction vessels, wherein each separate first stage reaction vessel comprises at least m*f solid phase synthesis units;
    (c) reacting the solid phase synthesis units in each of the separate first stage reaction vessels with a different first component in the first stage of the synthesis;
    (d) segregating the solid phase synthesis units of (c) into m separate second stage reaction vessels by distributing at least one of the solid phase synthesis units from each of the separate first stage vessels into each separate second stage reaction vessel such that each of the separate second stage reaction vessels comprises at least n*f solid phase synthesis units;
    (e) reacting the solid phase synthesis units in each of the separate second stage reaction vessels with a different second component in the second stage of the synthesis, thereby synthesizing the library of the materials;

(f) detecting one or more distinguishing physical properties of selected members of the library; and, (g) identifying the selected members based on the one or more detected distinguishing physical properties.

2. The method of claim 1, wherein the method is completely or partially computer implemented.

3. The method of claim 1, wherein each different first and second component independently comprises an organic or an inorganic component.

4. The method of claim 1, wherein the library of the materials comprises a combinatorial chemical library.

5. The method of claim 1, wherein the at least $n*m*f$ solid phase synthesis units are subjected to one or more split/pool synthesis steps prior to (a).

6. The method of claim 1, wherein the solid phase synthesis units each comprise a single particle independently selected from one or more of: a bead, a crown, a piece of paper, a piece of cotton, or a piece of polymer.

7. The method of claim 1, wherein one or more of the solid phase synthesis units comprise single functionalized particles.

8. The method of claim 1, wherein one or more of the solid phase synthesis units comprise single non-functionalized particles.

9. The method of claim 1, wherein at least two of the solid phase synthesis units comprise single particles having different functionalities attached thereto.

10. The method of claim 1, wherein at least one of the separate first stage reaction vessels comprises at least two solid phase synthesis units comprising different functionalities.

11. The method of claim 1, wherein each separate first stage reaction vessel in (b) comprises $m*f$ solid phase synthesis units.

12. The method of claim 1, wherein (b) comprises providing one or more of the at least $m*f$ solid phase synthesis units in one or more two-dimensional arrays in the separate first stage reaction vessels.

13. The method of claim 1 wherein one or more of the at least $m*f$ solid phase synthesis units in one or more of the separate first stage reaction vessels are non-arrayed.

14. The method of claim 1, wherein each of the separate second stage reaction vessels in (d) comprises $n*f$ solid phase synthesis units.

15. The method of claim 1, wherein (d) comprises providing one or more of the at least $n*f$ solid phase synthesis units in one or more two-dimensional arrays in the separate second stage reaction vessels.

16. The method of claim 1 wherein one or more of the at least $n*f$ solid phase synthesis units in one or more of the separate second stage reaction vessels are non-arrayed.

17. The method of claim 1, wherein the solid phase synthesis units of (d) are randomly arranged in at least one of the second stage reaction vessels.

18. The method of claim 1, wherein the solid phase synthesis units of (d) are non-randomly arranged in at least one of the second stage reaction vessels.

19. The method of claim 1, wherein each of the separate second stage reaction vessels designates which different second component reacted with the solid phase synthesis units therein to thereby permit structural identification of selected library members upon detecting the one or more distinguishing physical properties of the selected members in (f).

20. The method of claim 1, wherein the solid phase synthesis units each comprise multiple particles combined together.

21. The method of claim 20, wherein an array or a container comprises the multiple particles combined together.

22. The method of claim 20, wherein at least one of the multiple particles comprises a non-functionalized solid support.

23. The method of claim 20, wherein at least one of the multiple particles comprises a solid support having one or more functionalities attached thereto.

24. The method of claim 20, wherein at least two of the multiple particles comprise solid supports having one or more identical functionalities attached thereto.

25. The method of claim 20, wherein at least two of the multiple particles comprise solid supports having one or more different functionalities attached thereto.

26. The method of claim 1, wherein (a) comprises:

(i) segregating the at least $n*m*f$ solid phase synthesis units into p separate third stage reaction vessels, wherein p is equal to a number of choices of different third components in a third stage of the synthesis, and wherein each separate third stage reaction vessel comprises at least $n*m*f/p$ solid phase synthesis units;

(ii) reacting the solid phase synthesis units in each of the separate third stage reaction vessels with a different third component in the third stage of the synthesis; and, (iii) combining and mixing the solid phase synthesis units of (ii) in a single pool, thereby providing the at least $n*m*f$ solid phase synthesis units.

27. The method of claim 26, wherein the at least $n*m*f$ solid phase synthesis units comprise $n*m*f*p$ solid phase synthesis units.

28. The method of claim 26, further comprising:

(iv) separating the at least $n*m*f$ solid phase synthesis units of (iii) into $n*m$ separate containers, wherein the $n*m$ separate containers are segregated into the n separate first stage reaction vessels as the solid phase synthesis units of (b).

29. The method of claim 26, further comprising separating the at least $n*m*f$ solid phase synthesis units of (c) into $n*m$ separate containers, wherein the $n*m$ separate containers are segregated into the m separate second stage reaction vessels as the solid phase synthesis units of (d).

30. The method of claims 28 or 29, wherein each of the $n*m$ separate containers comprises multiple particles combined together.

31. The method of claim 1, wherein (f) further comprises cleaving the materials from the solid phase synthesis units prior to detecting the one or more distinguishing physical properties.

32. The method of claim 1, wherein the solid phase synthesis units of (e) each comprise multiple particles combined together, and wherein (f) further comprises separating selected particles from other particles and cleaving synthesized materials from the selected particles prior to detecting the one or more distinguishing physical properties.

33. The method of claims 1, 31, or 32, wherein the one or more distinguishing physical properties comprise different molecular masses.

34. The method of claim 33, wherein the different molecular masses are detected by mass spectrometry.

35. The method of claim 33, wherein structural identification of the selected members comprises determining a fingerprint of library members in one or more of the separate second stage reaction vessels.

36. The method of claim 33, wherein structural identification of the selected members comprises subtracting a mass of the different second component reacted in a particular separate second reaction vessel from the different detected masses of the selected members to thereby determine masses of different first components included in each of the selected members.

37. The method of claim 36, wherein the structural identification accounts for mass defects of reaction.

38. The method of claim 33, wherein structural identification of the selected members comprises correlating the different detected masses of the selected members to a physical or logical matrix comprising masses for each individual library member.

39. The method of claim 38, wherein at least one entry in the matrix comprises a summation of masses of different combinations of first and second components.

40. The method of claim 38, wherein correlations of the different detected masses to entries in the matrix account for mass defects of reaction.

41. The method of claim 38, wherein the correlation is computer implemented.

42. A combinatorial library synthesis system, comprising:
   (a) a plurality of reaction vessels;
   (b) a handling system configured to translocate solid phase synthesis units and reagents to and from the plurality of reaction vessels;
   (c) a detection system to detect one or more distinguishing physical properties of selected members of the combinatorial library; and,
   (d) a computer operably connected to the handling and detection systems, the computer comprising system software which directs the handling or detection systems to:
      (i) segregate the solid phase synthesis units into n separate first stage reaction vessels to provide $m*f$ solid phase synthesis units in each of the n vessels, wherein n is equal to a number of choices of different first components in a first stage of a library synthesis, m is equal to a number of choices of different second components in a second stage of the library synthesis, and f is equal to a number of solid phase synthesis units which comprise identical materials on completion of the library synthesis;
      (ii) deliver one or more of the different first components to each of the n separate first stage reaction vessels, thereby providing for reaction of the different first components with the solid phase synthesis units to provide first stage reacted solid phase members;
      (iii) segregate the first stage reacted solid phase members from the n separate first stage reaction vessels into m separate second stage reaction vessels by distributing at least one of the first stage reacted solid phase members from each of the separate first stage reaction vessels into each second stage reaction vessels such that each second stage reaction vessel comprises at least $n*f$ solid phase synthesis units;
      (iv) deliver one or more different second components to the second stage reaction vessels, thereby providing for reaction of the different second components with the first stage reacted solid phase members to provide the combinatorial library; and,
      (v) detect one or more distinguishing physical properties of the selected members of the combinatorial library.

43. The combinatorial library synthesis system of claim 42, wherein the handling system comprises a bead handler.

44. The combinatorial library synthesis system of claim 42, wherein prior to (i) the system software directs the handling system to:
   (1) segregate the at least $n*m*f$ solid phase synthesis units into p separate third stage reaction vessels, wherein p is equal to a number of choices of different third components in a third stage of the library synthesis, and wherein each separate third stage reaction vessel comprises at least $n*m*f/p$ solid phase synthesis units;
   (2) deliver one or more of the different third components to each of the separate third stage reaction vessels, thereby providing for reaction of the different third components with the solid phase synthesis units to provide third stage reacted solid phase members; and,
   (3) combine and mix the third stage reacted solid phase members in a single pool, thereby providing the solid phase synthesis units for (i).

45. The combinatorial library synthesis system of claim 44, wherein the at least $n*m*f$ solid phase synthesis units comprise $n*m*f*p$ solid phase synthesis units.

46. The combinatorial library synthesis system of claim 44, wherein the system software further directs the handling system to:
   (4) separate the solid phase synthesis units of (3) into $n*m$ separate containers, wherein the $n*m$ separate containers are segregated into the n separate first stage reaction vessels as the solid phase synthesis units of (i).

47. The combinatorial library synthesis system of claim 44, wherein the system software further directs the handling system to separate the solid phase synthesis units of (3) into $n*m$ separate containers, wherein the $n*m$ separate containers are segregated into the m separate second stage reaction vessels as the solid phase synthesis units of (iii).

48. The combinatorial library synthesis system of claims 46 or 47, wherein each of the $n*m$ separate containers comprises multiple particles combined together.

49. The combinatorial library synthesis system of claim 42, wherein the system software directs the handling system in (iv) to effect cleavage of combinatorial library members from the solid phase synthesis units.

50. The combinatorial library synthesis system of claims 42 or 49, wherein the one or more distinguishing physical properties comprise different masses.

51. The combinatorial library synthesis system of claim 50, wherein the detection system comprises a mass spectrometer.

52. The combinatorial library synthesis system of claim 51, wherein the computer further comprises at least one database having a logical matrix corresponding to masses of members of a virtual library that are correlated with the detected masses of the combinatorial library members produced by the system to thereby identify chemical structures of the combinatorial library members.

53. The combinatorial library synthesis system of claim 52, wherein correlations account for mass defects of reaction of the detected masses.

54. The combinatorial library synthesis system of claim 52, wherein at least one entry in the logical matrix comprises a summation of masses of different combinations of first and second components.

* * * * *